(12) United States Patent
Donde et al.

(10) Patent No.: US 9,637,467 B2
(45) Date of Patent: *May 2, 2017

(54) TREATMENT OF INFLAMMATORY BOWEL DISEASE

(71) Applicant: Allergan, Inc., Irvine, CA (US)

(72) Inventors: Yariv Donde, Dana Point, CA (US); Jeremiah H. Nguyen, La Puente, CA (US); Karen M. Kedzie, Rancho Santa Margarita, CA (US); Daniel W. Gil, Corona Del Mar, CA (US); John E. Donello, Dana Point, CA (US); Wha-Bin Im, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/846,016

(22) Filed: Sep. 4, 2015

(65) Prior Publication Data

US 2016/0096817 A1 Apr. 7, 2016

Related U.S. Application Data

(63) Continuation of application No. 14/268,264, filed on May 2, 2014, now Pat. No. 9,156,810, which is a continuation of application No. 12/945,013, filed on Nov. 12, 2010, now Pat. No. 8,754,122, which is a continuation of application No. 11/084,454, filed on Mar. 17, 2005, now Pat. No. 7,855,226, which is a continuation-in-part of application No. 10/365,369, filed on Feb. 11, 2003, now Pat. No. 6,875,787.

(51) Int. Cl.

| | | |
|---|---|---|
| *C07D 333/56* | (2006.01) | |
| *A61K 31/557* | (2006.01) | |
| *A61K 31/5575* | (2006.01) | |
| *C07D 333/62* | (2006.01) | |
| *C07D 409/08* | (2006.01) | |
| *A61K 31/559* | (2006.01) | |
| *C07C 59/90* | (2006.01) | |
| *C07C 69/732* | (2006.01) | |
| *C07C 57/26* | (2006.01) | |
| *C07C 57/48* | (2006.01) | |
| *C07C 69/738* | (2006.01) | |

(52) U.S. Cl.
CPC .......... *C07D 333/56* (2013.01); *A61K 31/557* (2013.01); *A61K 31/559* (2013.01); *A61K 31/5575* (2013.01); *C07C 57/26* (2013.01); *C07C 57/48* (2013.01); *C07C 59/90* (2013.01); *C07C 69/732* (2013.01); *C07C 69/738* (2013.01); *C07D 333/62* (2013.01); *C07D 409/08* (2013.01)

(58) Field of Classification Search
CPC .. C07D 333/56; C07D 333/62; C07D 409/08; A61K 31/557; A61K 31/5575; A61K 31/559; C07C 59/90; C07C 69/732; C07C 57/26; C07C 57/48; C07C 69/738
See application file for complete search history.

(56) References Cited

U.S. PATENT DOCUMENTS

| | | | |
|---|---|---|---|
| 4,117,014 A | 9/1978 | Pernet et al. | |
| 4,959,311 A | 9/1990 | Shih et al. | |
| 4,994,274 A | 2/1991 | Chan et al. | |
| 5,034,413 A | 7/1991 | Chan et al. | |
| 5,446,047 A | 8/1995 | Danishefsky et al. | |
| 6,437,146 B1 | 8/2002 | Hattori et al. | |
| 6,531,504 B2 * | 3/2003 | Burk ................... | A61K 31/381 514/438 |
| 6,710,072 B2 | 3/2004 | Burk et al. | |
| 6,875,787 B2 * | 4/2005 | Donde ............... | A61K 31/5575 514/385 |
| 7,439,386 B2 | 10/2008 | Donde | |
| 7,855,226 B2 * | 12/2010 | Donde ................ | A61K 31/557 514/443 |

(Continued)

FOREIGN PATENT DOCUMENTS

| | | |
|---|---|---|
| EP | 1097922 | 5/2001 |
| JP | 59101458 | 6/1984 |

(Continued)

OTHER PUBLICATIONS

George Patani & Edmond LaVoie, Bioisosterism: A Rational Approach in Drug Design, 96 Chem. Rev. 3147 (1996).*
Waterbury et al., EP 3, But nor EP 2, FP, or TP Prostanoid-Recepror Stimulation May Reduce Intraocular Pressure, Investigative Ophthalmology & Visual Science, Dec. 1990, pp. 2560-2567, vol. 31, No. 12.
Williams et al., Drug Receptors, Burger's Medicinal Chemistry and Drug Discovery,1995, pp. 349-355, Fifth Edition, vol. 1, Chapter Eleven.

(Continued)

*Primary Examiner* — Sean Basquill
(74) *Attorney, Agent, or Firm* — Jonathan Bass

(57) ABSTRACT

Disclosed herein is a method comprising administering a compound to a mammal suffering from an inflammatory bowel disease for the treatment of said disease, said compound having a structure according to Formula I Formula I

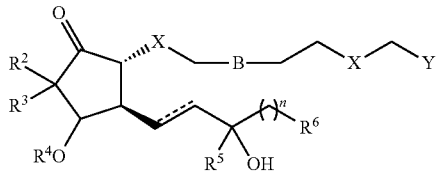

wherein X, Y, B, $R^2$, $R^3$, $R^4$, $R^5$, $R^6$ and n have the meanings found herein.

4 Claims, 9 Drawing Sheets

(56) References Cited

U.S. PATENT DOCUMENTS

Figure 1:
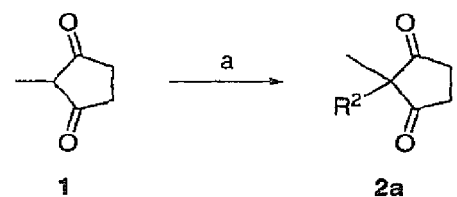
Figure 1:
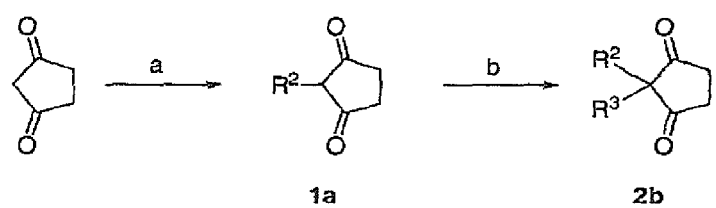
Figure 1:
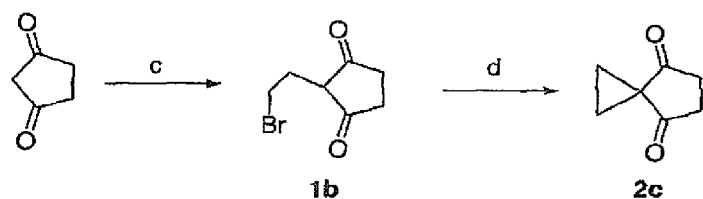

| | | | | |
|---|---|---|---|---|
| 7,872,045 | B2* | 1/2011 | Burk | A61K 31/557 514/530 |
| 7,893,107 | B2* | 2/2011 | Jiang | A61K 9/5078 514/443 |
| 8,754,122 | B2* | 6/2014 | Donde | A61K 31/557 514/517 |
| 9,156,810 | B2* | 10/2015 | Donde | A61K 31/557 |
| 2003/0027853 | A1 | 2/2003 | Burk et al. | |
| 2005/0222094 | A1 | 10/2005 | Burk et al. | |
| 2007/0123569 | A1 | 5/2007 | Jiang et al. | |
| 2010/0081631 | A1 | 4/2010 | Jiang et al. | |

FOREIGN PATENT DOCUMENTS

| | | | | |
|---|---|---|---|---|
| JP | 59101458 | * | 12/1984 | A61K 31/557 |
| JP | 63002972 | | 1/1988 | |
| JP | 63002972 | * | 1/1998 | A61K 31/557 |
| WO | 2004071428 | | 8/2004 | |

OTHER PUBLICATIONS

Briel et al., Biological Action and Half Life in Plasma of Intramuscular Sulprostone for Termination of Second Trimester Pregnancy, Prostaglandins and Medicine 6, 1981, pp. 1-8. West Germany.

K. Kabashima, et al., The prostaglandin receptor EP4 suppresses colitis, mucosal damage and CD4 cell activation in the gut, The Journal of Clinical Investigation, Apr. 2002, vol. 109, No. 7, p. 883-893.

Singer, et al, Cyclooxegynase 2 is Induced in Colonic Epithelial Cells in Inflammatory Bowel Disease, 115 Gastroenterology 297 (1998).

John Wallace, Prostaglandin Biology in Inflammatory Bowel Disease, 30 Gastroenterology Cun. N. Am. 971 (Dec. 2001).

Bruce E. Sands, Treatment of Inflammatory Bowel Disease, 118 Gastroenterology S68, S71 (Feb. 2000).

Daniel Podolsky, Inflammatory Bowel Disease, 347 N. Engl. J Med. 417, 417-21 (Aug. 8, 2002).

Nilsson et al, PGF2. Increases uveoscleral outflow, Invest Ophthalmol Vis Sci 1987; 28(3 Suppl) :284.

Brooks et al., Asymmetric Microbial Reduction of prochiral2,2-disubstituted cycloalkanediones, J. Org. Chern. 1987,52,3223-3232.

Bito L.Z., Prostaglandins, other eicosanoids, and their derivatives as potential antiglaucoma agents, Chap. 20, pp. 477-505, Glaucoma: Aprlied pharmacology in medical treatment, Grune & Stratton, Inc., S.Drance, et al., Editors. 1984.

Bito, L.Z., Prostaglandins and related compounds as potential ocular therapeutic agents, Chpt. 18, Biological Protection with Prostaglandins, vol. 1, CRC Press, Inc., M.M. Cohen, Editor. 1985.

Bito, L.Z., Prostaglandins old concepts and new perspectives, Arch Ophthalmol—vol. 105, Aug. 1987, pp. 1 036-1 0-39.

Patent Abstracts of Japan, vol. 0082, No. 18 (C-503), Jun. 10, 1988 & JP 63 002972 A (Nippon lyakuhin Kogyo KK), Jan. 7, 1988.

Hamon et al., Synthesis of (+-)- and 15-EPI(+-)-10, 10-Dimthylprostaglandin E1, Tetrahedron Letters, Elsevier Science Publishers, Amsterdam, NL, No. 3, Jan. 1976, pp. 211-214.

Plantema et al., Synthesis of 10,10-dimethylprostaglandin E1, Tetrahedron Letters, (51), 1975, 4039.

Plantema et al., Synthesis of (.+-.)-10.10-dimethylprostaglandin El methyl ester and its 15-epimer, Journal of the Chemical Society, Perkin Transactions 1: Organic and Bio-organic Chemistry (1972-1999), (3), 1978, pp. 304-308.

Pernet, Andre G. et al., Prostaglandin analogs modified at the 10 and 11 positions, Tetrahedron Letters, (41), 1979, pp. 3933-3936.

Burger, Alfred, Isosterism and Bioisosterism in Drug Design, Progress in Drug Research, 1991, pp. 287-328.

Patani et al., Bioisosterism: A Rational Approach in Drug Design, 96 Chem. Rev. 3147, 1996.

Patent Cooperation Treaty, Notification of Transmittal of the International Search Report and the Written Opinion of the International Searching Authority, or the Declaration, International Searching Authority, European Patent Office, Mar. 20, 2007.

* cited by examiner

Equation 1

Equation 2

Equation 3

(a) KOH, I-R$^2$, dioxane/H$_2$O;  (b) KOH, I-R$^3$, dioxane/H$_2$O;  (c) KOH, 1,2-dibromoethane, dioxane/H$_2$O;  (d) KOH, dioxane/H$_2$O.

(a) KOH, MeI, dioxane/H₂O; (b) Baker's Yeast, D-glucose, H₂O; (c) TBSOTf, 2,6-lutidine, CH₂Cl₂; (d) LDA, THF; PhSeCl; (e) 30% H₂O₂, CH₂Cl₂.

(a) NaH, BrCH$_2$CO$_2$CH$_3$; (b) H$_2$O$_2$, NaOH, MeOH; (c) basic Alumina, CH$_2$Cl$_2$.

(a) Cp$_2$ZrHCl, THF; (b) MeLi, Et$_2$O -78 °C; (c) lithium 2-thienycyanocuprate;
(d) enone 10, THF -78 °C; (e) HF-pyridine, CH$_3$CN; separate diastereomers
(i) rabbit liver esterase, phosphate buffer, CH$_3$CN.

(a) TBSCl, etc.; (b) n-BuLi; DMF; (c) Ac$_2$O, pyridine; (d) Jones oxidation; (e) MeOH, AcCl; (f) PPh$_3$, I$_2$, imidazole, CH$_2$Cl$_2$.

(a) t-BuLi, THF -78 °C; (b) Me$_2$Zn; (c) HF-pyridine, CH$_3$CN; separate diastereomers; (d) rabbit liver esterase, pH 7.2 phosphate buffer, CH$_3$CN; (e) NiCl$_2$, NaBH$_4$, ethylenediamine, H$_2$, THF;

(a) ClCO$_2$CH$_2$CH$_3$, Et$_3$N, CH$_2$Cl$_2$; NH$_4$OH $_{(aq)}$;
(b) EDCI, N-hydroxysuccinimide, H$_2$NCH$_2$CH$_2$OH, DMF.

(a) n-BuLi; ethylene oxide; (b) Dess-Martin [O]; (c) ethynylmagnesium bromide; (d) TBSCl, DMAP, Et₃N; (e) Cp₂ZrHCl; NIS.

TREATMENT OF INFLAMMATORY BOWEL DISEASE

CROSS-REFERENCE TO RELATED APPLICATIONS

This application is a continuation of U.S. patent application Ser. No. 14/268,264, filed May 2, 2014, which in turn is a continuation of U.S. patent application Ser. No. 12/945,013, filed Nov. 12, 2010, now U.S. Pat. No. 8,745,122 issued Jun. 17, 2014, which is a continuation of U.S. patent application Ser. No. 11/084,454, filed on Mar. 17, 2005, now U.S. Pat. No. 7,855,226, issued Dec. 21, 2010, which is a continuation-in-part of U.S. patent application Ser. No. 10/772,720, filed Feb. 4, 2004; which is a continuation-in-part of U.S. patent application Ser. No. 10/365,369, filed Feb. 11, 2003, now U.S. Pat. No. 6,875,787, issued Apr. 5, 2005, each of which are incorporated herein by reference in their entireties, and serve as the basis for a priority and/or benefit claim of the present application.

DESCRIPTION OF RELATED ART

Prostaglandins can be described as derivatives of prostanoic acid which have the following structural formula:

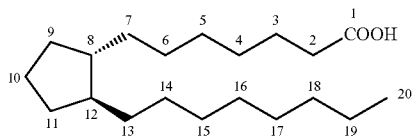 [SMILES: CCCCCCCC[C@H]1CCC[C@@H]1CCCCCCC(=O)O]

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandins are useful for the long-term medical management of glaucoma (see, for example, Bito, L. Z. *Biological Protection with Prostaglandins*, Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Certain 15,15-dimethyl prostaglandins with antihypertensive, gastric acid secretion inhibition, and smooth muscle stimulant properties, are known to have improved metabolic stability. These are described in documents such as the following:

Pernet et al in U.S. Pat. No. 4,117,014 (filed 23 Dec. 1976);
Pernet, Andre G. et al., Prostaglandin analogs modified at the 10 and 11 positions, Tetrahedron Letters, (41), 1979, pp. 3933-3936;
Plantema, Otto G. et al., Synthesis of (.+-.)-10.10-dimethylprostaglandin E1 methyl ester and its 15-epimer, Journal of the Chemical Society, Perkin Transactions 1: Organic and Bio-organic Chemistry (1972-1999), (3), 1978, pp. 304-308;
Plantema, O. G. et al., Synthesis of 10,10-dimethylprostaglandin E1, Tetrahedron Letters, (51), 1975, 4039;
Hamon, A., et al., Synthesis of (+-)- and 15-EPI(+-)-10,10-Dimthylprostaglandin E1, Tetrahedron Letters, Elsevier Science Publishers, Amsterdam, NL, no. 3, January 1976, pp. 211-214; and
Patent Abstracts of Japan, Vol. 0082, no. 18 (C-503), Jun. 10, 1988 & JP 63 002972 A (Nippon Iyakuhin Kogyo KK), 7 Jan. 1988;

the disclosure of these documents are hereby expressly incorporated by reference.

Inflammatory bowel disease (IBD) is a group of disease characterized by inflammation in the large or small intestines and is manifest in symptoms such as diarrhea, pain, and weight loss. Nonsteroidal anti-inflammatory drugs have been shown to be associated with the risk of developing IBD, and recently Kabashima and colleagues have disclosed that "EP4 works to keep mucosal integrity, to suppress the innate immunity, and to downregulate the proliferation and activation of CD4+ T cells. These findings have not only elucidated the mechanisms of IBD by NSAIDs, but also indicated the therapeutic potential of EP4-selective agonists in prevention and treatment of IBD." (Kabashima, et. al., The Journal of Clinical Investigation, April 2002, Vol. 9, 883-893)

SUMMARY OF THE INVENTION

Disclosed herein is a method comprising administering a compound to a mammal suffering from an inflammatory bowel disease for the treatment of said disease, said compound having a structure according to Formula I

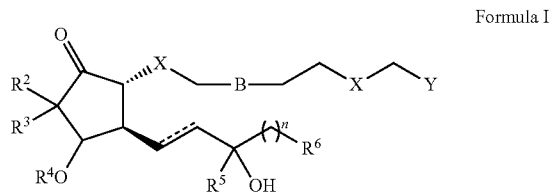

Formula I wherein the dashed line indicates the presence or absence of a bond, the hatched wedge indicates the α (down) configuration, and the solid triangle indicates the β (up) configuration;
B is a single, double, or triple covalent bond;
n is 0-6;
X is $CH_2$, S or O;
Y is any pharmaceutically acceptable salt of $CO_2H$, or $CO_2R$, $CONR_2$, $CONHCH_2CH_2OH$, $CON(CH_2CH_2OH)_2$, $CH_2OR$, $P(O)(OR)_2$, $CONRSO_2R$, $SONR_2$, or

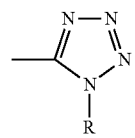

R is H, $C_{1-6}$ alkyl or $C_{2-6}$ alkenyl;
$R^2$ and $R^3$ are $C_{1-6}$ linear alkyl which may be the same or different, and may be bonded to each other such that they form a ring incorporating the carbon to which they are commonly attached;

$R^4$ is hydrogen, R, C(=O)R, or any group that is easily removed under physiological conditions such that $R^4$ is effectively hydrogen;

$R^5$ is hydrogen or R;

$R^6$ is
  i) hydrogen;
  ii) a linear or branched hydrocarbon containing between 1 and 8 carbon atoms, which may contain one or more double or triple bonds, or oxygen or halogen derivatives of said hydrocarbon, wherein 1-3 carbon or hydrogen atoms may be substituted by O or a halogen; or
  iii) aryloxy, heteroaryloxy, $C_{3-8}$ cycloalkyloxy, $C_{3-8}$ cycloalkyl, $C_{6-10}$ aryl or $C_{3-10}$ heteroaryl, wherein one or more carbons is substituted with N, O, or S; and which may contain one or more substituents selected from the group consisting of halogen, trihalomethyl, cyano, nitro, amino, hydroxy, $C_{6-10}$ aryl, $C_{3-10}$ heteroaryl, aryloxy, heteroaryloxy, $C_{1-6}$ alkyl, OR, SR, and $SO_2R$.

Compositions and medicaments related thereto are also disclosed.

DESCRIPTION OF THE DRAWING FIGURES

Figure 2:
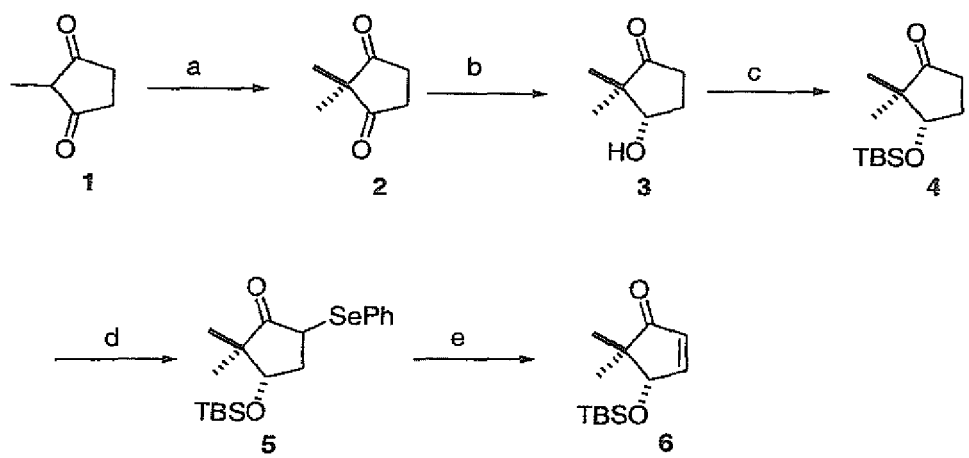
Figure 3:
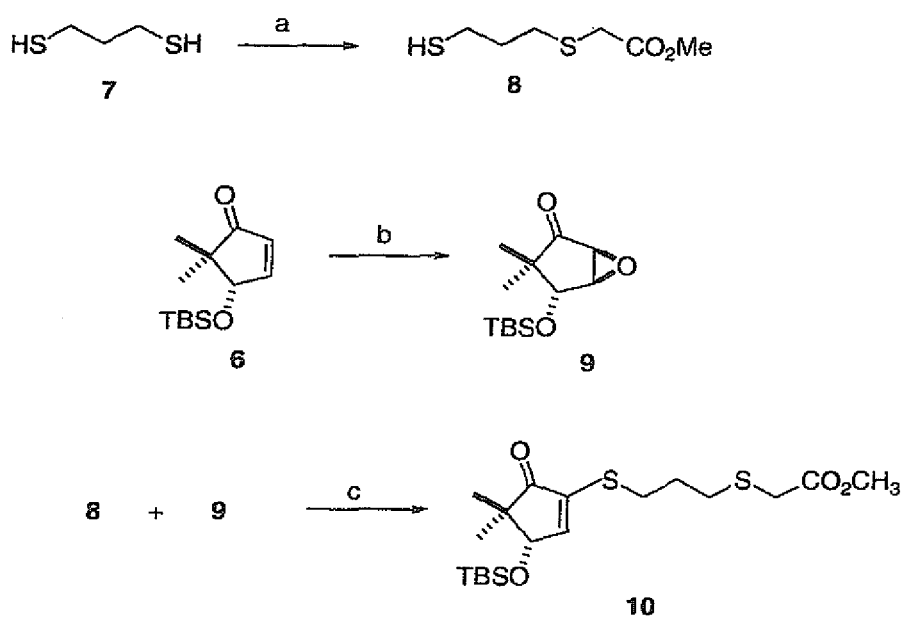
Figure 4:
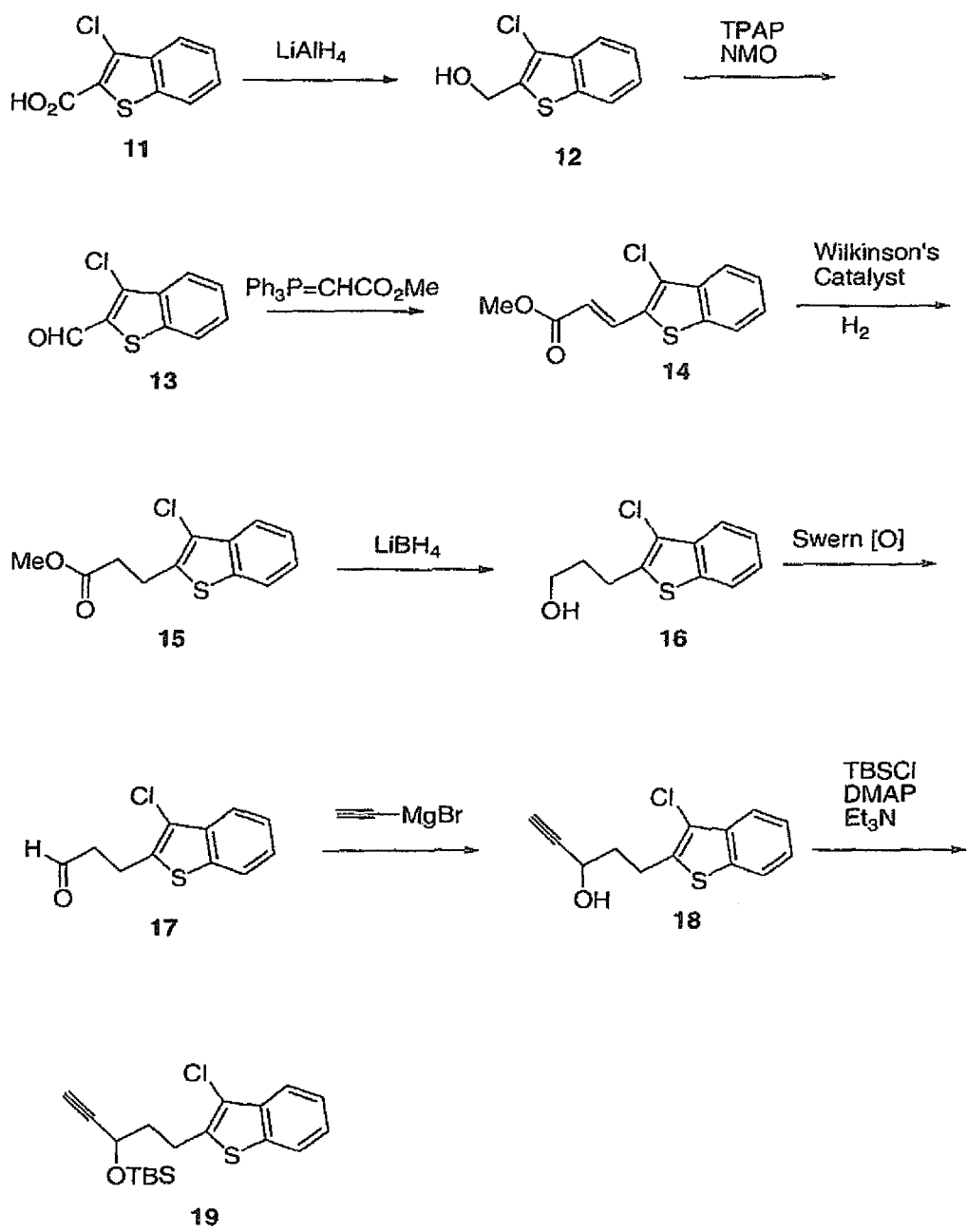
Figure 5:
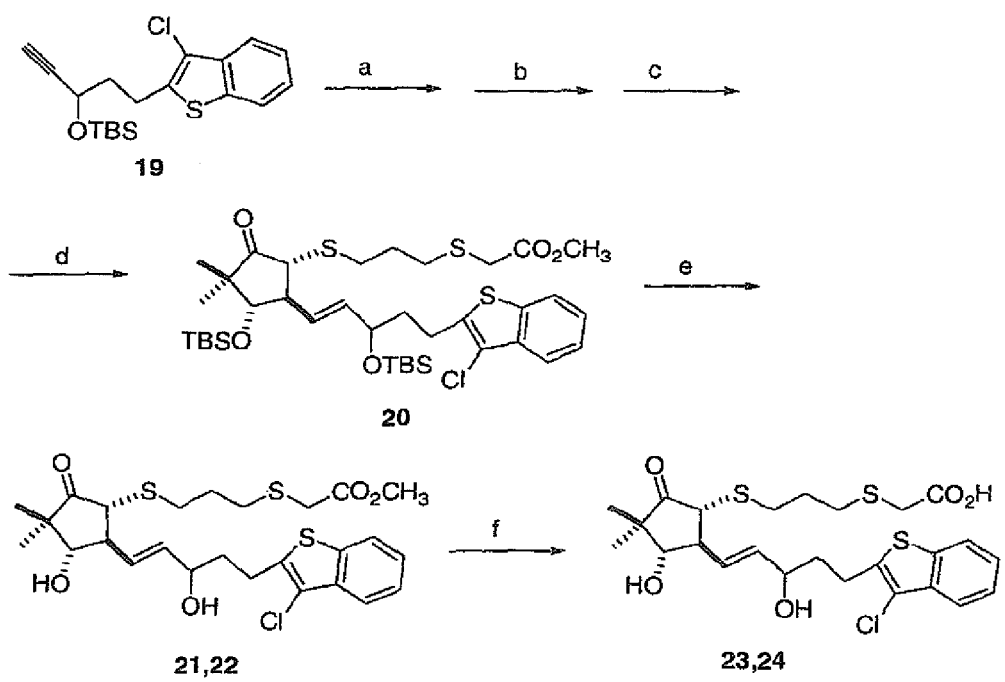
Figure 6:
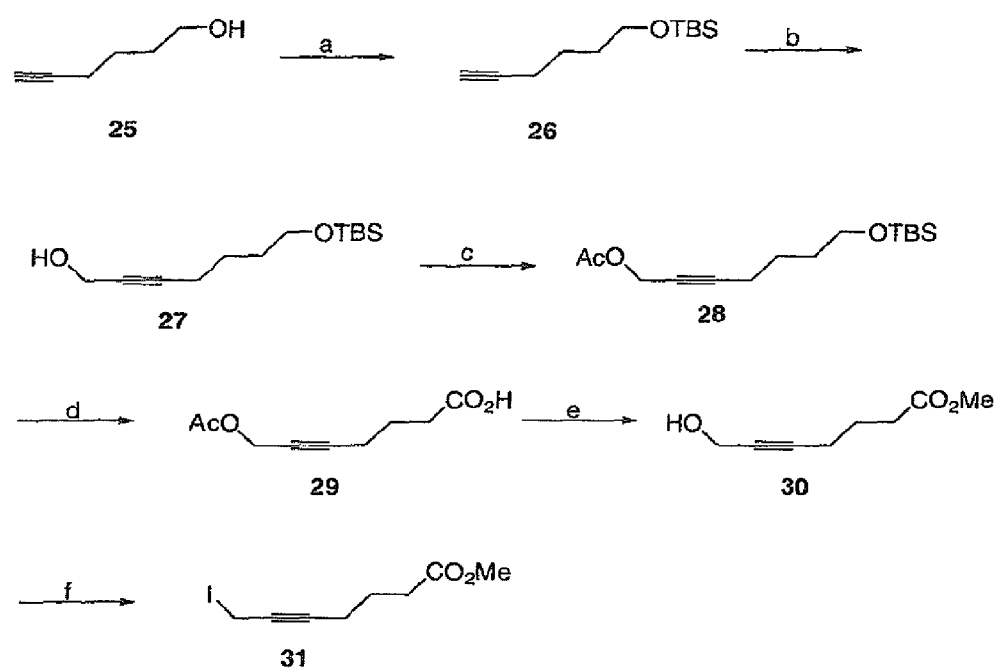
Figure 7:
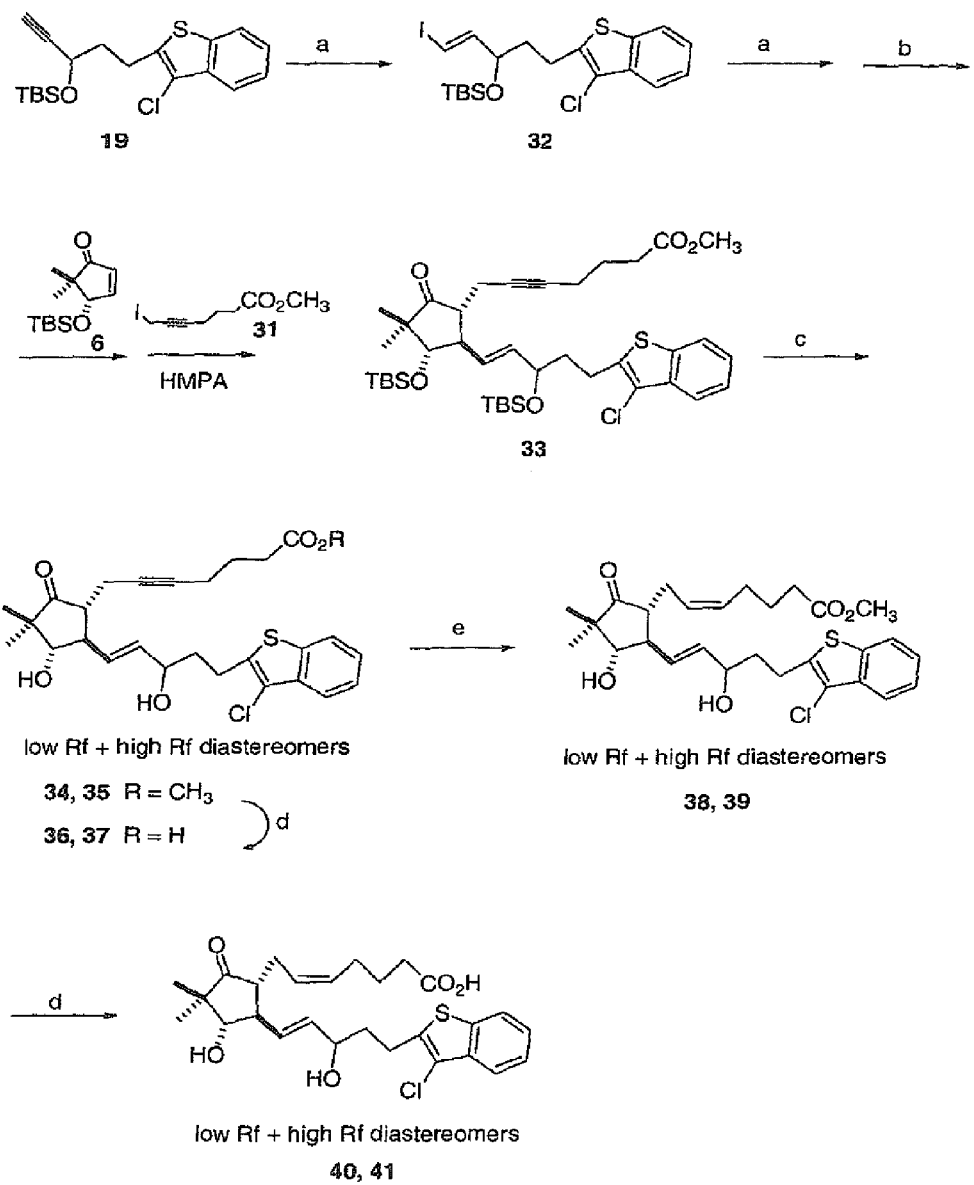
Figure 8:
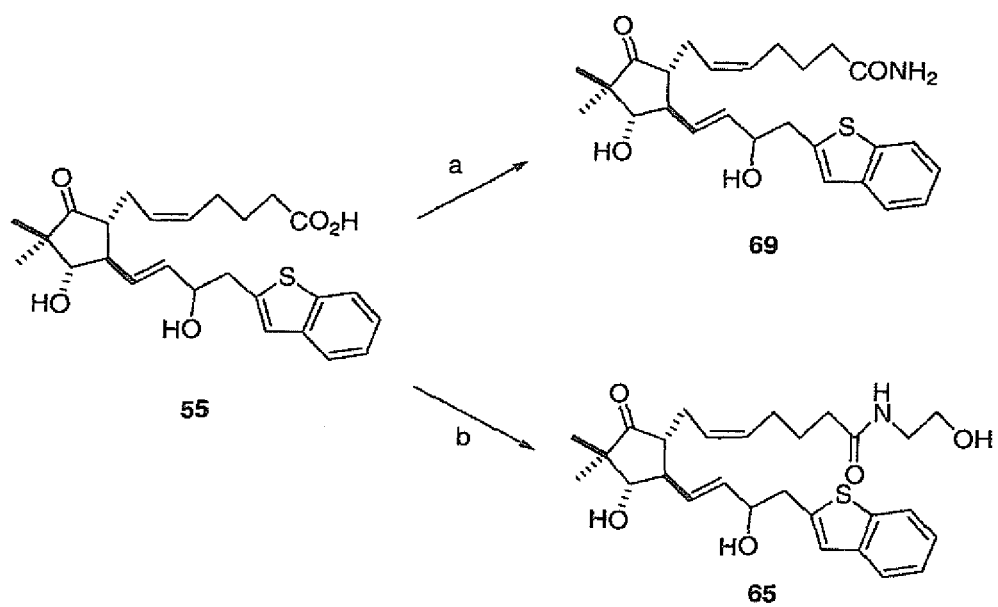
Figure 9:
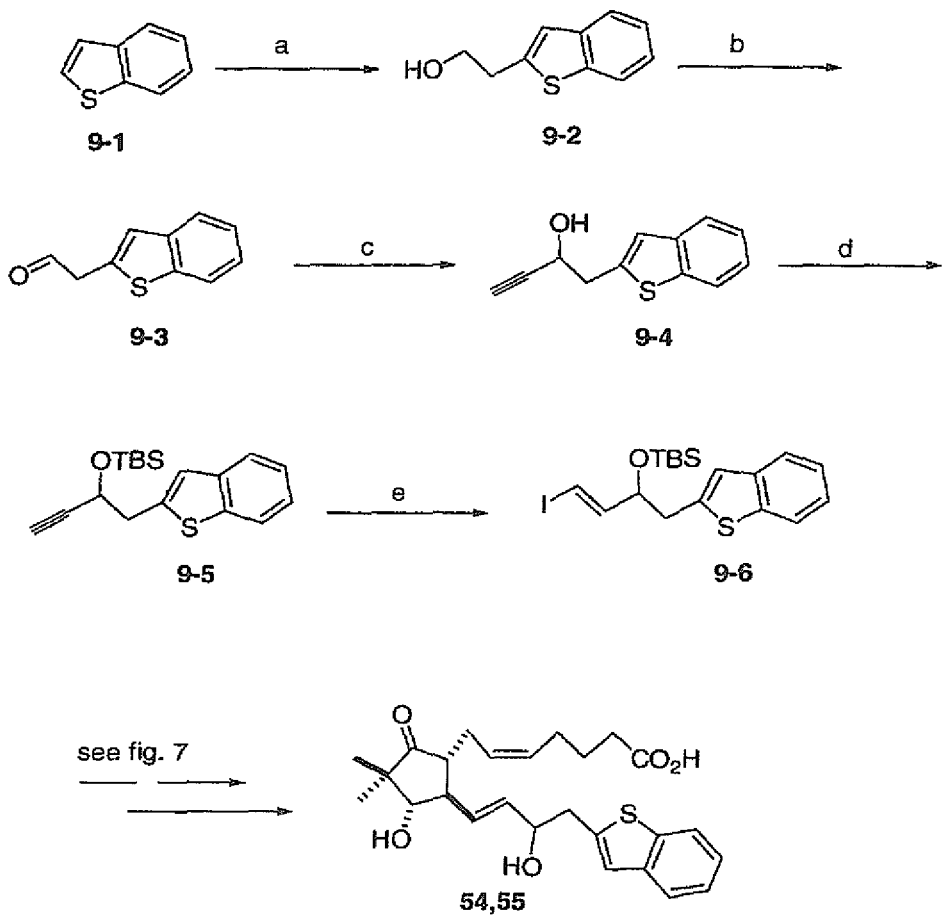

FIGS. 1-9 illustrate possible ways to prepare compounds of the invention.

DETAILED DESCRIPTION OF THE INVENTION

Treatment of inflammatory bowel disease may be accomplished by the administration of the compounds described herein to the suffering mammal Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

The compounds used in the treatment described herein have a structure according to Formula I

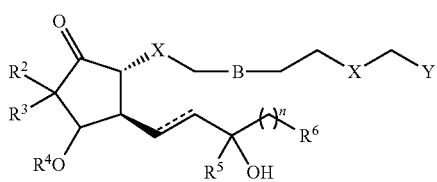

Formula I

A preferred group of the compounds of the present invention includes compounds that do not have the following structural formula II:

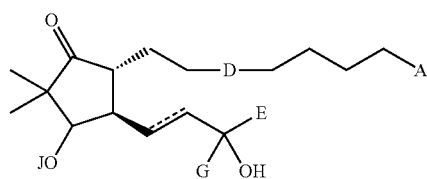

Formula II wherein A is $CO_2H$, $CO_2Me$, or $CO_2Et$;

D is a single, double, or triple covalent bond;

E is a linear, branched, or cycloalkyl chain of 3 to 7 carbons, trifluoromethylbutyl, hydroxylalkyl, or $CH_2R^7$ wherein $R^7$ is phenyl, cyclopentyl, phenoxy, chlorophenoxy, propoxy, or —$CH_2SCH_2CH_3$;

J is hydrogen, R, C(=O)R, or any group that is easily removed under physiological conditions such that $R^4$ is effectively hydrogen; and G is H or $CH_3$.

As used herein, the symbols "Me" and "Et" refer to the moieties commonly referred to as "methyl" and "ethyl" by those of ordinary skill in the art.

In other compounds related to Formula I and Formula II, A is $CO_2R^8$, wherein $R^8$ is any linear, branched, or cyclic alkyl group having from 3 to 6 carbons.

Another preferred group includes compounds having formula III:

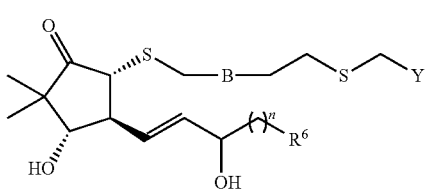

Formula III

Another preferred group includes compounds having formula IV:

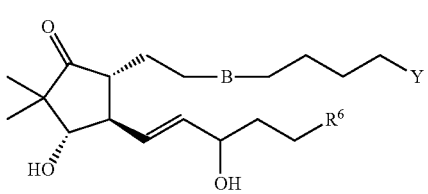

Formula IV

Another preferred group includes compounds having formula V:

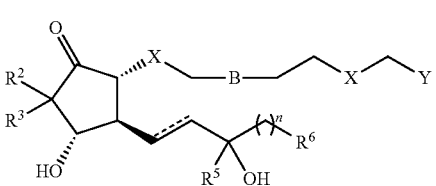

Formula V wherein at least one of $R^2$ and $R^3$ is not methyl.

In the above formulae, the substituents and symbols are as hereinabove defined. In the above formulae:

Preferably Y is any pharmaceutically acceptable salt of $CO_2H$ or $CO_2R$. More preferably Y is $CO_2H$ or $CO_2Me$.

Preferably n is 2.

Preferably, $R^6$ is $C_{6-10}$ aryl or $C_{3-10}$ heteroaryl, which may contain one or more substituents selected from the group consisting of halogen, trihalomethyl, cyano, nitro, amino, hydroxy, $C_{1-6}$ alkyl, OR, SR, and $SO_2R$. More preferably $R^6$ is phenyl, napthyl, benzofuranyl, or benzothienyl, which may contain one or more substituents selected from the group consisting of halogen, trihalomethyl, cyano, nitro, amino, hydroxy, $C_{1-6}$ alkyl, OR, SR, and $SO_2R$. Most preferred is 3-chlorobenzothien-2-yl.

Another preferred group includes compounds having formula XIII:

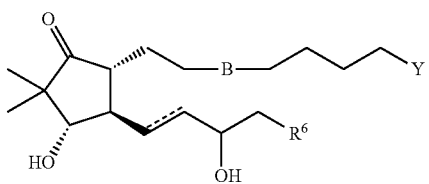

Formula XIII wherein B represents a single or double bond;
and $R^6$ is napthyl, benzofuranyl, or benzothienyl, which may contain one or more substituents selected from the group consisting of halogen, trihalomethyl, cyano, nitro, amino, hydroxy, $C_{1-6}$ alkyl, OR, SR, and $SO_2R$.

Compounds useful for the methods described herein may be prepared by methods known to those skilled in the art. The synthesis of several of these compounds is illustrated in Schemes 2-7. These Schemes that are included herein are merely illustrative and are not intended to limit the scope of the invention in any way. Although there are several ways the reduction of compounds of Formula VI to Formula VII could be incorporated into the synthesis of these compounds, one convenient way to this is shown in Scheme 2. In this Scheme, compound 2 is a compound of Formula VI and compound 3 is a compound of formula VII. However, those skilled in the art will recognize that there are many ways in which the reduction could be used to prepare compounds of this invention.

TABLE 1

| Structure | Low Rf diastereomer | High Rf diastereomer |
| --- | --- | --- |
| 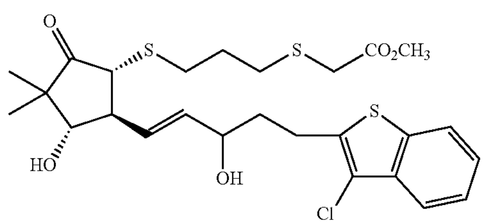 [SMILES: COC(=O)CSCCCS[C@H]1C(=O)C(C)(C)[C@@H](O)[C@@H]1/C=C/C(O)CCc1sc2ccccc2c1Cl] | 21 | 22 |
| 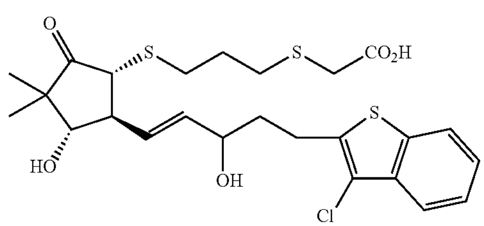 [SMILES: CC1(C)C(=O)[C@H](SCCCSCC(=O)O)[C@@H](/C=C/C(O)CCc2sc3ccccc3c2Cl)[C@@H]1O] | 23 | 24 |
| 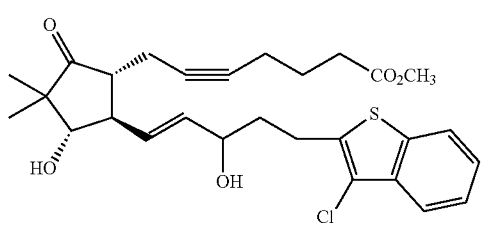 [SMILES: COC(=O)CCCC#CC[C@H]1C(=O)C(C)(C)[C@@H](O)[C@@H]1/C=C/C(O)CCc1sc2ccccc2c1Cl] | 34 | 35 |
| 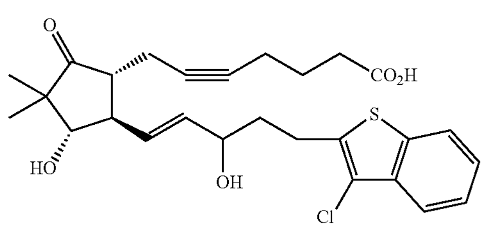 [SMILES: CC1(C)C(=O)[C@H](CC#CCCCC(=O)O)[C@@H](/C=C/C(O)CCc2sc3ccccc3c2Cl)[C@@H]1O] | 36 | 37 |

TABLE 1-continued

| Structure | Low Rf diastereomer | High Rf diastereomer |
|---|---|---|
| 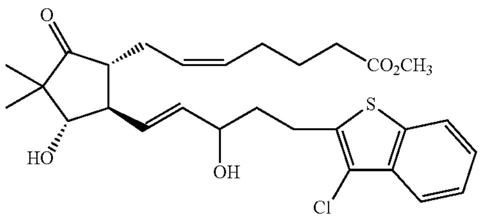 [SMILES: COC(=O)CCC/C=C\C[C@H]1C(=O)C(C)(C)[C@@H](O)[C@@H]1/C=C/C(O)CCc1sc2ccccc2c1Cl] | 38 | 39 |
| 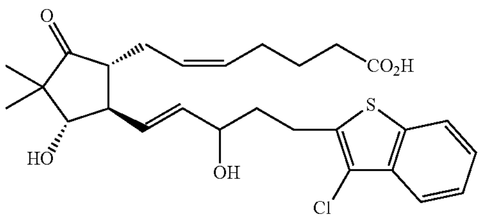 [SMILES: CC1(C)C(=O)[C@H](C/C=C\CCCC(=O)O)[C@@H](/C=C/C(O)CCc2sc3ccccc3c2Cl)[C@@H]1O] | 40 | 41 |
| 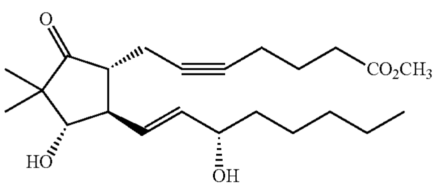 [SMILES: CCCCC[C@H](O)/C=C/[C@@H]1[C@@H](CC#CCCCC(=O)OC)C(=O)C(C)(C)[C@H]1O] | 42 | |
| 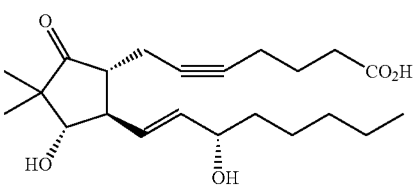 | 43 | |
| 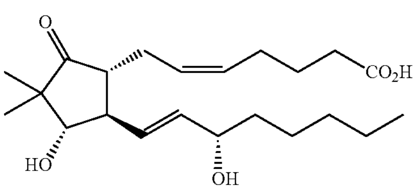 [SMILES: CCCCC[C@H](O)/C=C/[C@@H]1[C@@H](C/C=C\CCCC(=O)O)C(=O)C(C)(C)[C@H]1O] | 44 | |
| 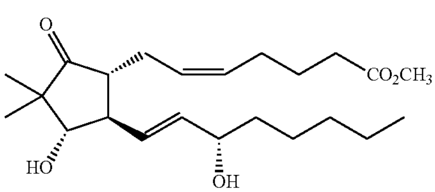 [SMILES: CCCCC[C@H](O)/C=C/[C@@H]1[C@@H](C/C=C\CCCC(=O)OC)C(=O)C(C)(C)[C@H]1O] | 45 | |
| 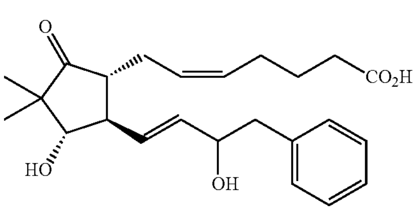 [SMILES: CC1(C)C(=O)[C@H](C/C=C\CCCC(=O)O)[C@@H](/C=C/C(O)Cc2ccccc2)[C@@H]1O] | 46 | 47 |

TABLE 1-continued
| Structure | Low Rf diastereomer | High Rf diastereomer |
|---|---|---|
| 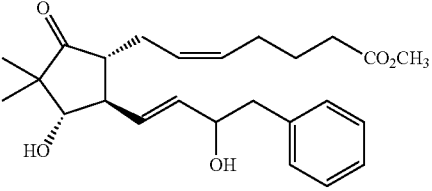 [SMILES: COC(=O)CCC/C=C\C[C@H]1C(=O)C(C)(C)[C@@H](O)[C@@H]1/C=C/C(O)Cc1ccccc1] | 48 | 49 |
| 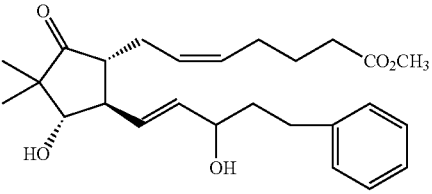 [SMILES: COC(=O)CCC/C=C\C[C@H]1C(=O)C(C)(C)[C@@H](O)[C@@H]1/C=C/C(O)CCc1ccccc1] | 50 | 51 |
| 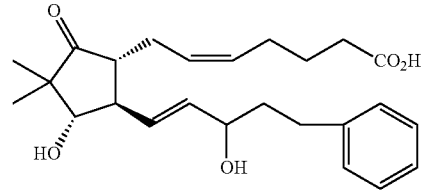 [SMILES: CC1(C)C(=O)[C@H](C/C=C\CCCC(=O)O)[C@@H](/C=C/C(O)CCc2ccccc2)[C@@H]1O] | 52 | 53 |
| 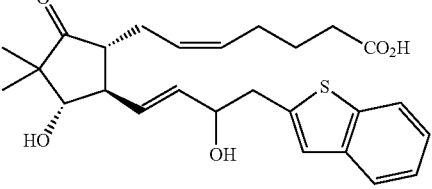 | 54 | 55 |
| 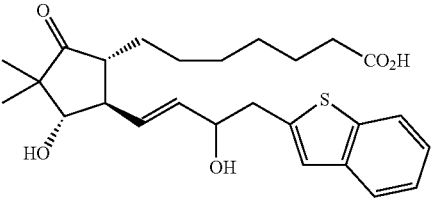 [SMILES: CC1(C)C(=O)[C@H](CCCCCCC(=O)O)[C@@H](/C=C/C(O)Cc2cc3ccccc3s2)[C@@H]1O] | 56 | 57 |
| 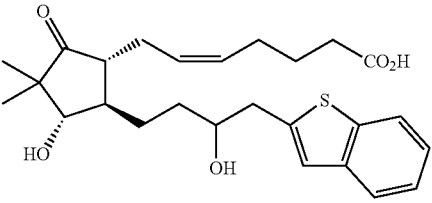 [SMILES: CC1(C)C(=O)[C@H](C/C=C\CCCC(=O)O)[C@@H](CCC(O)Cc2cc3ccccc3s2)[C@@H]1O] | 58 | 59 |
| 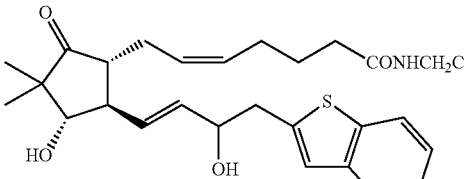 | 60 | 61 |

TABLE 1-continued

| Structure | Low Rf diastereomer | High Rf diastereomer |
|---|---|---|
| (structure with CON(CH₂CH₃)₂) | 62 | 63 |
| (structure with CONHCH₂CH₂OH) | 64 | 65 |
| (structure with tetrazole) | 66 | 67 |
| (structure with CONH₂) | 68 | 69 |
| (structure with CO₂CH₃, cis alkene) | 70 | 71 |
| (structure with CO₂CH₃, alkyne) | 72 | 73 |
| (structure with CO₂H, alkyne) | 74 | 75 |

The compounds named below, and illustrated in Table 1, are especially preferred representatives of the compounds of the present invention:

(3-{(1R,4S,5S)-5-(3-chloro-benzo[b]thiophen-2-yl)-3-hydroxy-pent-1-enyl]-4-hydroxy-3,3-dimethyl-2-oxo-cyclopentylsulfanyl}-propylsulfanyl)-acetic acid methyl ester (21, 22);

(3-{(1R,4S,5S)-5-(3-chloro-benzo[b]thiophen-2-yl)-3-hydroxy-pent-1-enyl]-4-hydroxy-3,3-dimethyl-2-oxo-cyclopentylsulfanyl}-propylsulfanyl)-acetic acid (23, 24);

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-ynoic acid methyl ester (34, 35);

(Z)-7-{(1R,4S,5R)-5-[(E)-5-(3-chloro-benzo [b]thiophene-2-yl)-3-hydroxy-pent-1-enyl]-4-hydroxy-3,3-dimethyl-2-oxo-cyclopentyl}1-hept-5-ynoic acid (36,37);

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid methyl ester (38,39);

(Z)-7-{(1R,4S,5R)-5-[(E)-5-(3-chloro-benzo [b]thiophene-2-yl)-3-hydroxy-pent-1-enyl]-4-hydroxy-3,3-dimethyl-2-oxo-cyclopentyl}-hept-5-enoic acid (40,41);

7-[(1R,4S,5R)-4-Hydroxy-5-((E)-(S)-3-hydroxy-oct-1-enyl)-3,3-dimethyl-2-oxo-cyclopentyl]-hept-5-ynoic acid methyl ester (42)

7-[(1R,4S,5R)-4-Hydroxy-5-((E)-(S)-3-hydroxy-oct-1-enyl)-3,3-dimethyl-2-oxo-cyclopentyl]-hept-5-ynoic acid (43)

(Z)-7-[(1R,4S,5R)-4-Hydroxy-5-((E)-(S)-3-hydroxy-oct-1-enyl)-3,3-dimethyl-2-oxo-cyclopentyl]-hept-5-enoic acid (44)

(Z)-7-[(1R,4S,5R)-4-Hydroxy-5-((E)-(S)-3-hydroxy-oct-1-enyl)-3,3-dimethyl-2-oxo-cyclopentyl]-hept-5-enoic acid methyl ester (45)

(Z)-7-[(1R,4S,5R)-4-Hydroxy-5-((E)-3-hydroxy-4-phenyl-but-1-enyl)-3,3-dimethyl-2-oxo-cyclopentyl]-hept-5-enoic acid (46, 47)

(Z)-7-[(1R,4S,5R)-4-Hydroxy-5-((E)-3-hydroxy-4-phenyl-but-1-enyl)-3,3-dimethyl-2-oxo-cyclopentyl]-hept-5-enoic acid methyl ester (48, 49)

(Z)-7-[(1R,4S,5R)-4-Hydroxy-5-((E)-3-hydroxy-5-phenyl-pent-1-enyl)-3,3-dimethyl-2-oxo-cyclopentyl]-hept-5-enoic acid methyl ester (50, 51)

(Z)-7-[(1R,4S,5R)-4-Hydroxy-5-((E)-3-hydroxy-5-phenyl-pent-1-enyl)-3,3-dimethyl-2-oxo-cyclopentyl]-hept-5-enoic acid (52, 53)

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid (54, 55)

7-[(1R,4S,5R)-5-((E)-4-Benzo[b]thiophen-2-yl-3-hydroxy-but-1-enyl)-4-hydroxy-3,3-dimethyl-2-oxo-cyclopentyl]-heptanoic acid (56, 57)

(Z)-7-[(1R,4S,5R)-5-(4-Benzo[b]thiophen-2-yl-3-hydroxy-butyl)-4-hydroxy-3,3-dimethyl-2-oxo-cyclopentyl]-hept-5-enoic acid (58, 59)

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid ethylamide (60, 61)

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid diethylamide (62, 63)

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid (2-hydroxy-ethyl)-amide (64, 65)

(3S,4R,5R)-4-((E)-4-Benzo[b]thiophen-2-yl-3-hydroxy-but-1-enyl)-3-hydroxy-2,2-dimethyl-5-[(Z)-6-(1-H-tetrazol-5-yl)-hex-2-enyl]-cyclopentanone (66, 67)

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid amide (68, 69)

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid methyl ester (70, 71)

7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-ynoic acid methyl ester (72, 73)

7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-ynoic acid (74, 75)

Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

SYNTHETIC EXAMPLES

The methods of preparing compounds of this invention are further illustrated by the following non-limiting Examples, which are summarized in the reaction schemes of FIGS. 1-7 wherein the compounds are identified by the same designator in both the Examples and the Figures.

2-Alkyl-cyclopentane-1,3-dione (1a). A mixture of 1,3-cyclopentanedione (89.4 mmol, Aldrich), I—$R^2$ (96.4 mmol, Aldrich), and KOH (5.097 g, 90.8 mmol) in $H_2O$ (25 mL)/dioxane (75 mL) is heated at reflux. After 5 h, a solution of KOH (2 g) and I—$R^2$ (2 mmol) in $H_2O$ (5 mL)/dioxane (15 mL) is added and after another 3 h at reflux the solution is allowed to stir at room temperature overnight. In the morning, the reaction is continued by addition of a solution of KOH (2 g) and I—$R^2$ (2 4 mmol) in $H_2O$ (5 mL)/dioxane (15 mL) and heating at reflux. After 4 h, the mixture is allowed to cool to room temperature and is extracted with ether (1×100 mL, 3×75 mL). The combined ether extracts are evaporated, the residue is combined with HCl (50 mL 10%), and the resulting mixture is placed in a 120° C. oil bath until boiling is observed (ca. 15 min.). The mixture is then allowed to cool to room temperature, is neutralized by addition of $NaHCO_3$ solution (150 mL, saturated) and the resulting mixture is then extracted with $CH_2Cl_2$ (4×75 mL). The combined $CH_2Cl_2$ solution is dried ($MgSO_4$), filtered and evaporated to leave a brown oil which is used directly in the next step.

2-Alkyl-2-methyl-cyclopentane-1,3-dione (2a). A mixture of 2-methyl-1,3-cyclopentanedione (10.025 g, 89.4 mmol, Aldrich), I—$R^2$ (96 4 mmol, Aldrich), and KOH (5.097 g, 90.8 mmol) in $H_2O$ (25 mL)/dioxane (75 mL) is heated at reflux. After 5 h, a solution of KOH (2 g) and I—$R^2$ (2 mmol) in $H_2O$ (5 mL)/dioxane (15 mL) is added and after another 3 h at reflux the solution is allowed to stir at room temperature overnight. In the morning, the reaction is continued by addition of a solution of KOH (2 g) and I—$R^2$ (2.4 mmol) in $H_2O$ (5 mL)/dioxane (15 mL) and heating at reflux. After 4 h, the mixture is allowed to cool to room temperature and is extracted with ether (1×100 mL, 3×75 mL). The combined ether extracts are evaporated, the residue is combined with HCl (50 mL 10%), and the resulting mixture is placed in a 120° C. oil bath until boiling is observed (ca. 15 min.). The mixture is then allowed to cool to room temperature, is neutralized by addition of $NaHCO_3$ solution (150 mL, saturated) and the resulting mixture is then extracted with $CH_2Cl_2$ (4×75 mL). The combined $CH_2Cl_2$ solution is dried ($MgSO_4$), filtered and evaporated to leave a brown oil which is used directly in the next step.

2,2-Dialkyl-methyl-cyclopentane-1,3-dione (2b). A mixture of 2-alkyl-1,3-cyclopentanedione 1a (89.4 mmol, Aldrich), I—$R^3$ (96.4 mmol, Aldrich), and KOH (5.097 g, 90.8 mmol) in $H_2O$ (25 mL)/dioxane (75 mL) is heated at reflux. After 5 h, a solution of KOH (2 g) and I—$R^3$ (2 mmol) in $H_2O$ (5 mL)/dioxane (15 mL) is added and after another 3 h at reflux the solution is allowed to stir at room temperature overnight. In the morning, the reaction is continued by addition of a solution of KOH (2 g) and I—$R^3$ (2 4 mmol) in $H_2O$ (5 mL)/dioxane (15 mL) and heating at reflux. After 4 h, the mixture is allowed to cool to room temperature and is extracted with ether (1×100 mL, 3×75 mL). The combined ether extracts are evaporated, the residue is combined with HCl (50 mL 10%), and the resulting mixture is placed in a 120° C. oil bath until boiling is observed (ca. 15 min.). The mixture is then allowed to cool to room temperature, is neutralized by addition of $NaHCO_3$ solution (150 mL, saturated) and the resulting mixture is then extracted with $CH_2Cl_2$ (4×75 mL). The combined $CH_2Cl_2$ solution is dried ($MgSO_4$), filtered and evaporated to leave a brown oil which is used directly in the next step.

Spiro[2.4]heptane-4,7-dione (2c). A mixture of 2-alkyl-1,3-cyclopentanedione 1a (89.4 mmol, Aldrich), 1,2-dibromoethane (120 mmol, Aldrich), and KOH (5.097 g, 90.8 mmol) in $H_2O$ (25 mL)/dioxane (75 mL) is heated at reflux for 24 hours. The mixture is allowed to cool, and the crude product is extracted with ether (1×100 mL, 3×75 mL). The combined ether extracts are evaporated, the residue is combined with HCl (50 mL 10%), and the resulting mixture is placed in a 120° C. oil bath until boiling is observed (ca. 15 min.). The mixture is then allowed to cool to room temperature, is neutralized by addition of $NaHCO_3$ solution (150 mL, saturated) and the resulting mixture is then extracted with $CH_2Cl_2$ (4×75 mL). The combined $CH_2Cl_2$ solution is dried ($MgSO_4$), filtered and evaporated to leave a brown oil which is used directly in the next step.

2,2-Dimethyl-cyclopentane-1,3-dione (2). The published procedure was followed. (Agosta, W. C.; Smith, A. B. *J. Org. Chem.* 1970, 35, 3856) A mixture of 2-methyl-1,3-cyclopentanedione (10.025 g, 89.4 mmol, Aldrich), methyl iodide (6.0 mL, 96 4 mmol, Aldrich), and KOH (5.097 g, 90.8 mmol) in $H_2O$ (25 mL)/dioxane (75 mL) was heated at reflux. After 5 h, a solution of KOH (2 g) and MeI (2.4 mL) in $H_2O$ (5 mL)/dioxane (15 mL) was added and after another 3 h at reflux the solution was allowed to stir at room temperature overnight. In the morning, the reaction was continued by addition of a solution of KOH (2 g) and MeI (2.4 mL) in $H_2O$ (5 mL)/dioxane (15 mL) and heating at reflux. After 4 h, the mixture was allowed to cool to room temperature and was extracted with ether (1×100 mL, 3×75 mL). The combined ether extracts were evaporated, the residue combined with HCl (50 mL 10%), and the resulting mixture was placed in a 120° C. oil bath until boiling was observed (ca. 15 min.). The mixture was then allowed to cool to room temperature, was neutralized by addition of $NaHCO_3$ solution (150 mL, saturated) and the resulting mixture then extracted with $CH_2Cl_2$ (4×75 mL). The combined $CH_2Cl_2$ solution was dried ($MgSO_4$), filtered and evaporated to leave a brown oil (10.474 g, 83 mmol, 93%) which was used directly in the next step.

(S)-3-Hydroxy-2,2-dimethyl-cyclopentanone (3). The published procedure was followed. (Brooks, D. W.; Hormoz, M.; Grothaus, P. G. J. Org. Chem. 1987, 52, 3223) A 35° C. (internal temperature) solution of D-glucose (106.73 g, 592 mmol, Aldrich) in $H_2O$ (690 mL) in a 4 L Erlenmeyer was treated with baker's yeast (71.065 g, Fleischmann's). The mixture was allowed to ferment for 2 h, then 2,2-dimethyl-cyclopentane-1,3-dione (2) (7.316 g, 58 mmol) was added.

The mixture was stirred for 48 h and then filtered through celite, washing with about 1 L $CH_2Cl_2$. The filtration was difficult due to the thick consistency of the yeast and it helped to continually add $CH_2Cl_2$ to the mixture and scrape the top of the celite layer with a spatula. The filtrate was transferred to a separatory funnel, and 100 mL brine was added and the layers were separated. Brine (400 mL) was added to the aqueous layer and the resulting solution extracted further with $CH_2Cl_2$ (3×500 mL). The combined $CH_2Cl_2$ solution was dried ($MgSO_4$), filtered and evaporated to leave a yellow oil. Flash chromatography (11×5 cm, 20% EtOAc/hexs→25%→30%→40%→50%) gave alcohol 3 (2.435 g, 19 mmol, 33%).

The enantiomeric excess of 3 was assayed by $^1H$ NMR of the corresponding Mosher's ester which was prepared by treatment of alcohol 3 (11 mg, 0.09 mmol) in dichloroethane (0.3 mL, Aldrich) with pyridine (27 μL, 0.33 mmol, Aldrich) and (R)-α-methoxy-α-trifluoromethyphenylacetic acid chloride (58 μL, 0.31 mmol, Fluka). The mixture was stirred overnight and then partitioned between water (10 mL) and ether (10 mL). The ether layer was washed with 1 M HCl (10 mL) and saturated $NaHCO_3$ solution and then was dried ($MgSO_4$), filtered and evaporated. $^1H$ NMR analysis was done on the crude ester.

(S)-3-(tert)-Butyl-dimethyl-silanyloxy-2,2-dimethyl-cyclopentanone (4). A solution of alcohol 3 (520 mg, 4.1 mmol) and 2,6-lutidine (0.56 mL, 4.8 mmol, Aldrich) in $CH_2Cl_2$ (8.0 mL, Aldrich) was treated with TBSOTf (1.0 mL, 4.3 mmol, Aldrich). After 5.5 h, saturated $NaHCO_3$ solution (20 mL) was added and the mixture extracted with $CH_2Cl_2$ (20 mL). The $CH_2Cl_2$ solution was washed with 20 mL each of 1 M HCl, saturated $NaHCO_3$ solution, and brine and then was dried ($MgSO_4$), filtered and evaporated. Flash chromatography (5×5 cm, 10% $Et_2O$/pentane) gave TBS ether 4 (698 mg, 2.9 mmol, 70%).

(S)-3-(tert)-Butyl-dimethyl-silanyloxy-2,2-dimethyl-5-phenylselanyl-cyclopentanone (5). A solution of TBS ether 4 (1.496 g, 6.2 mmol) in THF (2 mL, Aldrich) was added dropwise to a −78° C. solution of LDA (4.9 mL, 7.3 mmol, 1.5 M/cyclohexane, Aldrich) in THF (22 mL, Aldrich), rinsing with 2 mL THF. After 15 min., a solution of PhSeCl (1.424 g, 7.4 mmol, Aldrich) in THF (2 mL) was quickly added by cannula, rinsing with 2 mL THF. The solution was stirred for 10 min. and then partitioned between 50 mL 0.5 M HCl and 75 mL ether. The ether layer was washed with 30 mL each of water, saturated $NaHCO_3$ solution, and brine and then was dried ($MgSO_4$), filtered and evaporated. Flash chromatography (2% EtOAc/hexs→4%) gave phenylselenide 5 (1.641 g, 4.1 mmol, 67%) along with 476 mg of mixed fractions containing a lower $R_f$ impurity.

(S)-4-(tert)-Butyl-dimethyl-silanyloxy-5,5-dimethyl-cyclopent-2-enone(6). A solution of selenide 5 (1.641 g, 4.1 mmol) and pyridine (0.62 mL, 7 7 mmol, Aldrich) in $CH_2Cl_2$ (13 mL, Aldrich) was treated with $H_2O$ (1 mL) and 30% $H_2O_2$ (1.1 mL, Aldrich). The mixture was stirred for 30 min. and then was partitioned between 25 mL $CH_2Cl_2$ and 25 mL saturated $NaHCO_3$ solution. The aqueous layer was extracted with 25 mL $CH_2Cl_2$ and the combined $CH_2Cl_2$ solution washed with 1 M HCl (2×25 mL) and brine (50 mL). The solution was then dried ($MgSO_4$), filtered and evaporated to leave an orange oil. Flash chromatography (6×4 cm, 10% ether/pentane) gave enone 6 (572 mg, 2.4 mmol, 59%).

(3-Mercapto-propylsulfanyl)-acetic acid methyl ester (8). An ice-cold solution of 1,3-dithiane (2.0 mL, 19.9 mmol) in THF (40 mL) was treated with NaH (819 mg, 20.5 mmol). After 30 min., methyl bromoacetate (1.9 mL, 20.0 mmol) was added and the mixture stirred for 3.5 h at room temperature. The reaction was quenched by addition of MeOH and then 50 mL 1 M HCl. The mixture was extracted with ether (2×50 mL) and the combined ether solution washed with saturated sodium bicarbonate solution (50 mL) and brine (50 mL) and then was dried ($MgSO_4$), filtered and evaporated. Purification by flash chromatography on silica gel (10-15% ethyl acetate/hexanes) gave 971 mg (5.38 mmol, 27%) of the thiol.

{3-[(S)-3-(tert)-Butyl-dimethyl-silanyloxy)-4,4-dimethyl-5-oxo-cyclopent-1-enylsulfanyl]-propylsulfanyl}-acetic acid methyl ester (10). A solution of enone 6 (156 mg, 0.65 mmol) in MeOH (4.3 mL) was treated with 30% $H_2O_2$ (0.21 mL) and 1 M NaOH (32 μL). After 4 h, 20 mL saturated ammonium chloride solution was added and the mixture was extracted with dichloromethane (3×10 mL). The combined dichloromethane solution was dried ($Na_2SO_4$), filtered and evaporated in vacuo.

A solution of thiol 8 (110 mg, 0.61 mmol) in dichloromethane (3 mL) was added to the crude epoxide (9) by cannula, rinsing with 1.2 mL. Basic alumina (628 mg) was added and the mixture stirred for 16 h. The solvent was evaporated and purification of the residue by flash chromatography on silica gel (15% ethyl acetate/hexanes) gave 129 mg (0.31 mmol, 48%) of the coupled enone (10).

(3-Chloro-benzo[b]thiophen-2-yl)-methanol (12). To an ice cold solution of 10.0 g (47.0 mmol) of 3-chloro-benzo[b]thiophene-2-carboxylic acid (11) in 200 mL of THF was added 47 mL of $LiAlH_4$ (47 mmol, 1 M/THF). After 3 h, the reaction was quenched by addition of MeOH (ca. 40 mL). The volatiles were evaporated and the residue was treated with 50 mL 1 M HCl. After stirring for 10 min., the mixture was extracted with $CH_2Cl_2$ (3×150 mL). The combined $CH_2Cl_2$ solution was dried ($MgSO_4$), filtered and evaporated. Purification by flash chromatography on silica gel (10-20% ethyl acetate/hexane) gave 4.32 g (21.6 mmol, 46%) of the alcohol (12).

3-Chloro-benzo[b]thiophene-2-carbaldehyde (13). A solution of alcohol 12 (4.32 g, 21.6 mmol) in 40 mL of $CH_2Cl_2$ was treated with 4A molecular sieves, NMO (3.81 g, 32.5 mmol), and TPAP (381 mg, 1.08 mmol). The reaction was stirred for 10 min. and then was evaporated to dryness. Purification by flash chromatography on silica gel (2% ethyl acetate/hexane) gave 3.52 g (18.3 mmol, 84%) of the aldehyde (13).

(E)-3-(3-Chloro-benzo[b]thiophen-2-yl)-acrylic acid methyl ester (14). A solution of 3.52 g (18.3 mmol) of 13 in 50 mL toluene was treated with methyl(triphenylphosphoranylidene)acetate (7.48 g, 21.9 mmol). After 4 h, saturated $NaHCO_3$ solution (50 mL) was added and the mixture extracted with ethyl acetate (2×75 mL). The combined ethyl acetate solution was washed with brine (50 mL), dried ($Na_2SO_4$), filtered and evaporated. Purification by flash chromatography on silica gel (5% ethyl acetate/hexane) provided 3.60 g (14.6 mmol, 80%) of the enoate (14).

3-(3-Chloro-benzo[b]thiophen-2-yl)-propionic acid methyl ester (15). A solution of 3.60 g (14.6 mmol) of 14 in 50 mL THF was treated with Wilkinson's catalyst (3.35 g, 3.62 mmol). The mixture was stirred under 1 atm $H_2$ for 18 h and then was filtered through celite. The solvent was evaporated and the residue purified by flash chromatography on silica gel (0-2% ethyl acetate/hexane) to give 3.63 g (14.3 mmol, 99%) of the saturated ester (15).

3-(3-Chloro-benzo[b]thiophen-2-yl)-propan-1-ol (16). An ice cold solution of 3.63 g (14.3 mmol) of 15 in 60 mL of ether was treated with LiBH$_4$ (621 mg, 28.5 mmol) and methanol (2 mL). After 30 min., 30 mL of 0.5 M NaOH solution was added. The mixture was extracted with ethyl acetate (2×25 mL) and the combined ethyl acetate solution washed with brine (50 mL), dried (MgSO$_4$), filtered and evaporated. The residue was purified by flash chromatography on silica gel (5-20% ethyl acetate/hexane) to give 2.57 g (11 3 mmol, 79%) of the alcohol (16).

3-(3-Chloro-benzo[b]thiophen-2-yl)-propionaldehyde (17). A −78° C. solution of oxalyl chloride (1.73 g, 13.6 mmol) in dichloromethane (20 mL) was treated with DMSO (20 mL). After 5 min., a solution of alcohol 16 (2.57 g, 11.3 mmol) in dichloromethane (20 mL) was added. After another 15 min., triethylamine (7.1 mL, 50.6 mmol) was added. The reaction was stirred at −78° C. for 5 min., and then allowed to warm to room temperature. After 30 min., 100 mL water was added and the mixture extracted with dichloromethane (3×60 mL). The combined dichloromethane solution was dried (Na$_2$SO$_4$), filtered and evaporated. Purification by flash chromatography on silica gel (10% ethyl acetate/hexane) gave 2.11 g (9.4 mmol, 83%) of the aldehyde (17).

5-(3-Chloro-benzo[b]thiophen-2-yl)-pent-1-yn-3-ol (18). A solution of aldehyde 17 (2.11 g, 9.4 mmol) in 15 mL THF was added to a solution of ethynylmagnesium bromide (28.2 mL, 14.1 mmol, 0.5 M THF) at 0° C. After 1.5 h, saturated NH$_4$Cl solution (75mL) was added and the mixture was extracted with ethyl acetate (3×50 mL). The combined ethyl acetate solution was washed with brine (50 mL) and then was dried (Na$_2$SO$_4$), filtered and evaporated. Purification by flash chromatography (5-20% ethyl acetate/hexane) gave 2.20 g (8.78 mmol, 93%) of the alcohol (18).

tert-Butyl-{1-[2-(3-chloro-benzo[b]thiophen-2-yl)-ethyl]-prop-2-ynyloxy}-dimethyl-silane (19). A solution of alcohol 18 (2.20 g, 8.78 mmol) in dichloromethane (15 mL) was treated with DMAP (215 mg, 1.8 mmol), TBSCl (1.59 g, 10.5 mmol), and triethylamine (1.8 mL, 13.2 mmol). The reaction was stirred for 24 h and then saturated sodium bicarbonate solution (50 mL) was added. The mixture was extracted with dichloromethane (2×50 mL) and the combined dichloromethane solution dried (Na$_2$SO$_4$), filtered and evaporated. Purification by flash chromatography (4% ethyl acetate/hexane) gave 3.06 g (6.4 mmol, 73%) of the protected alcohol (19).

(3-{(1R,4S,5S)-4-(tert-Butyl-dimethyl-silanyloxy)-5-[(E)-3-(tert-butyl-dimethyl-silanyloxy)-5-(3-chloro-benzo[b]thiophen-2-yl)-pent-1-enyl]-3,3-dimethyl-2-oxo-cyclopentylsulfanyl}-propylsulfanyl)-acetic acid methyl ester (20). A solution of alkyne 19 (105 mg, 0.28 mmol) in THF (1.2 mL) was treated with bis(cyclopentadienyl)zirconium chloride hydride (91 mg, 0.35 mmol). The reaction was stirred for 30 min., then was cooled to −78° C. and treated with methyllithium (0.46 mL, 0.64 mmol, 1.4 M in ether). After 10 min., a precooled (−78° C.) solution of lithium 2-thienylcyanocuprate (1.3 mL, 0.33 mmol, 0.25 M in THF) was added by cannula. The reaction was stirred for 45 min. and then enone 10 (61 mg, 0.15 mmol) in 0.2 mL THF was added by cannula, rinsing with 0.2 mL THF. After 1 h, The reaction was quenched by addition of 20 mL 1:1 saturated ammonium chloride solution/concentrated ammonium hydroxide. The mixture was stirred for 45 min. and then was extracted with ethyl acetate (3×20 mL). The combined ethyl acetate solution was dried (Na$_2$SO$_4$), filtered and evaporated. Purification by flash chromatography on silica gel (10% ethyl acetate/hexanes) gave 51 mg (0.064 mmol, 43%) of the coupled product (20).

(3-{(1R,4S,5S)-5-(3-chloro-benzo[b]thiophen-2-yl)-3-hydroxy-pent-1-enyl]-4-hydroxy-3,3-dimethyl-2-oxo-cyclopentylsulfanyl}-propylsulfanyl)-acetic acid methyl ester (21, 22). A solution of 20 (51 mg, 0.064 mmol) in CH$_3$CN (1.6 mL) was treated with HF-pyridine (0.26 mL). The reaction was stirred for 24 h and then was quenched by addition of 15 mL saturated sodium bicarbonate solution. The mixture was extracted with dichloromethane (3×10 mL) and the combined dichloromethane solution was dried (Na$_2$SO$_4$), filtered and evaporated. Purification by preparative thin layer chromatography on silica gel (40% ethyl acetate/hexanes) gave 12 mg (0.023 mmol, 71%) of each diastereomer.

(3-{(1R,4S,5S)-5-(3-chloro-benzo[b]thiophen-2-yl)-3-hydroxy-pent-1-enyl]-4-hydroxy-3,3-dimethyl-2-oxo-cyclopentylsulfanyl}-propylsulfanyl)-acetic acid (23, 24). Rabbit liver esterase (9 mg) was added to a solution of the lower R$_f$ ester 21 (11 mg, 0.021 mmol) in pH 7.2 phosphate buffer (0.5 mL)/CH$_3$CN (0.1 mL). The mixture was stirred overnight and then 10 mL 0.5 M HCl was added along with a few mL's of brine. The mixture was extracted with ethyl acetate (3×10 mL) and the combined ethyl acetate solution dried (Na$_2$SO$_4$), filtered and evaporated. Purification by flash chromatography on silica gel (3-5% MeOH/CH$_2$Cl$_2$) gave 4 mg (0.0078 mmol, 37%) of the acid (23). 300 MHz $^1$H NMR (CDCl$_3$, ppm) δ 7.73 (2 H, d, J=8.4 Hz) 7.4-7.3 (2 H, m) 5.9-5.8 (1 H, m) 5.8-5.7 (1 H, m) 4.4-4.3 (1 H, m) 3.63 (1 H, d, J=9.7 Hz) 3.21 (2 H, s) 3.1-2.4 (11 H, overlapping m) 2.1-1.7 (4 H, overlapping m) 1.12 (3 H, s) 1.03 (3 H, s).

The higher R$_f$ ester was hydrolyzed similarly except a solution of rabbit liver esterase (10 mg) in 0.5 mL of pH 7.2 phosphate buffer was added to a solution of the ester (10 mg, 0.019 mmol) in CH$_3$CN (0.2 mL). The reaction was stirred for 22 h and then worked up and purified as above. This gave 7 mg (0.013 mmol, 71%) of the acid (24). 300 MHz $^1$H NMR (CDCl$_3$, ppm) δ 7.73 (2 H, d, J=8.8 Hz) 7.44-7.31 (2 H, m) 5.9-5.8 (1 H, m) 5.8-5.7 (1 H, m) 4.4-4.3 (1 H, m) 3.64 (1 H, d, J=9.7 Hz) 3.3-2.3 (13 H, overlapping m) 2.1-1.7 (4 H, overlapping m) 1.12 (3 H, s) 1.03 (3 H, s).

tert-Butyl-hex-5-ynyloxy-dimethyl-silane (26).

7-(tent-Butyl-dimethyl-silanyloxy)-hept-2-yn-1-ol (27).

Acetic acid 7-(tert-butyl-dimethyl-silanyloxy)-hept-2-ynyl ester (28). A solution of 7-(tert-Butyl-dimethyl-silanyloxy)-hept-2-yn-1-ol 27 (4.507 g, 21 mmol) in pyridine (20 mL) was treated with acetic anhydride (3.0 mL, 31.8 mmol). After 18 h, the solvent was evaporated and the residue co-evaporated with toluene. The residue was used directly in the next step.

7-Acetoxy-hept-5-ynoic acid (29). A solution of crude 28 in acetone (100 mL) was treated with Jones Reagent (18.0 mL, 41.4 mmol, 2.3 M). The mixture became warm and so was cooled with an ice bath. After 1 h at room temperature, 10 mL isopropyl alcohol was added and the mixture stirred further for 15 min. The mixture still had a brown color so another 10 mL isopropyl alcohol was added. After another 15 min., the color had not changed so the mixture was filtered through celite and the filtrate evaporated in vacuo. The residue was partitioned between 100 mL ether and 100 mL saturated ammonium chloride solution. The aqueous layer was extracted with 100 mL ether and the combined ether solution washed with brine and then was dried (MgSO$_4$), filtered and evaporated to leave a yellow oil (6.333 g) that was used directly in the next step.

7-Hydroxy-hept-5-ynoic acid methyl ester (30). The crude acid 29 (6.333 g) was treated with a 1% solution of acetyl chloride in methanol (60 mL). After 16 h, sodium bicarbonate (1.966 g, 23.4 mmol) was added. The mixture was dried (MgSO$_4$), filtered through celite and evaporated in vacuo. Purification by flash chromatography on silica gel (30-40% ethyl acetate/hexanes) gave 7-Hydroxy-hept-5-ynoic acid methyl ester 30 (3.022 g, 19.3 mmol, 92% from 7-(tert-Butyl-dimethyl-silanyloxy)-hept-2-yn-1-ol 27).

7-Iodo-hept-5-ynoic acid methyl ester (31). A solution of 30 (1.347 g, 8.6 mmol) in 5 mL dichloromethane was added to a mixture of triphenylphosphine (2.725 g, 10.4 mmol), imidazole (726 mg, 10.7 mmol), and iodine (2.602 g, 10.3 mmol) in 34 mL dichloromethane, rinsing with 5 mL dichloromethane. After 40 min., the dichloromethane was evaporated in vacuo to a few mL's and the resulting mixture filtered through basic alumina, washing with 10% ethyl acetate/hexanes. Purification by flash chromatography on silica gel (10% ethyl acetate/hexanes) gave 1.878 g (7.1 mmol, 83%) of the propargyl iodide.

tert-Butyl-{(E)-1-[2-(3-chloro-benzo[b]thiophen-2-yl)-ethyl]-3-iodo-allyloxy}-dimethyl-silane (32). A solution of alkyne 19 (5.547 g, 15.2 mmol) in dichloromethane (50 mL) was treated with Cp$_2$ZrHCl (5.794 g, 22.5 mmol). The reaction was stirred for 45 min. and then N-iodosuccinimide (4.966 g, 22.1 mmol) was added. After 15 min., saturated sodium bicarbonate solution (200 mL) was added and the mixture was extracted with dichloromethane (2×100 mL). The combined dichloromethane solution was dried (MgSO$_4$), filtered and evaporated. Purification by flash chromatography on silica gel (0-5% ethyl acetate/hexanes) gave 6.608 g (13.1 mmol, 86%) of the vinyl iodide (32).

7-{(1R,4S,5R)-4-(tert-Butyl-dimethyl-silanyloxy)-5-[(E)-3-(tert-butyl-dimethyl-silanyloxy)-5-(3-chloro-benzo[b]thiophen-2-yl)-pent-1-enyl]-3,3-dimethyl-2-oxo-cyclopentyl}-hept-5-ynoic acid methyl ester (33). A −78° C. solution of iodide 32 (675 mg, 1.34 mmol) in THF (2.0 mL) was treated with tert-butyllithium (1.73 mL, 2.94 mL, 1.7 M/pentane). The dark red mixture was stirred for 25 min. and then dimethylzinc (0.80 mL, 1.6 mmol, 2 M/toluene) was added. The solution was stirred at 0° C. for 15 min. and then recooled to −78° C. At this time, a solution of enone 6 (208 mg, 0.87 mmol) in THF (1.0 mL) was added over 2 h by syringe pump, rinsing with 0.5 mL THF. After 30 min., HMPA (1.34 mL, distilled from CaH$_2$) was added followed by a solution of propargyl iodide 31 (1.286 g, 4.83 mmol) in THF (1.0 mL). The solution was stirred in a −40° C. bath overnight and then 20 mL saturated ammonium chloride solution and 10 mL water were added. The mixture was extracted with dichloromethane (20 mL) and ethyl acetate (2×20 mL). The combined organic extracts were dried (MgSO$_4$), filtered and evaporated. Purification by flash chromatography on silica gel (5-10% ethyl acetate/hexanes) gave 198 mg (0.27 mmol, 31%) of 33.

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-ynoic acid methyl ester (34, 35). A solution of 33 (198 mg, 0.27 mmol) in CH$_3$CN (6.5 mL) was treated with HF-pyridine (1.2 mL). The solution was stirred for 3 h and saturated sodium bicarbonate solution (120 mL) was added. The mixture was extracted with dichloromethane (3×50 mL) and the combined dichloromethane solution dried (Na$_2$SO$_4$), filtered and evaporated. Purification by flash chromatography (50% ethyl acetate/hexane) followed by preparative TLC (55% ethyl acetate/hexane) gave 55 mg (0.11 mmol, 41%) of the less polar diastereomer (34) and 51 mg (0.10 mmol, 37%) of the more polar diastereomer (35).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-ynoic acid (low R$_f$ diastereomer, 36). A solution of 34 (9 mg, 0.017 mmol) and rabbit liver esterase (1 mg) in pH 7.2 phosphate buffer (2 mL)/CH$_3$CN (0.1 mL) was stirred for 17 h. The mixture was then coevaporated with CH$_3$CN to remove water and the residue purified by flash chromatography on silica gel (3-7% MeOH/CH$_2$Cl$_2$) to give 8 mg (0.016 mmol, 93%) of the acid (36).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-ynoic acid (high R$_f$ diastereomer, 37). A solution of 35 (12 mg, 0.023 mmol) and rabbit liver esterase (1 mg) in pH 7.2 phosphate buffer (2 mL)/CH$_3$CN (0.1 mL) was stirred for 17 h. TLC showed the presence of starting material, so another 2 mg of the esterase was added. After stirring for another 24 h, the reaction was complete. Work up and purification as above for 36 gave 8 mg (0.016 mmol, 69%) of the acid (37).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid methyl ester (low R$_f$ diastereomer, 38). Ethanol (95%, 2.5 mL) was added to NiCl$_2$ (50 mg, 0.39 mmol) and NaBH$_4$ (7 mg, 0.19 mmol). The resulting black mixture was stirred for 5 min. and then ethylenediamine (41 µL, 0.61 mmol) was added. After 15 min., a solution of alkyne 34 (40 mg, 0.077 mmol) in 0.5 mL 95% ethanol was added, rinsing with 0.5 mL ethanol. The flask was purged with H$_2$ and allowed to stir under 1 atm H$_2$ for 22 h. The mixture was then filtered through celite and purified by flash chromatography on silica gel (55% ethyl acetate/hexanes) to give 17 mg (0.032 mmol, 43%) of the alkene (38).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid methyl ester (high R$_f$ diastereomer 39). The same procedure as for 36 was followed to give 17 mg (0.032 mmol, 41%) of 39.

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid (low R$_f$ diastereomer, 40). The same procedure as above for 36 was used to give 9 mg (0.018 mmol, 85%) of acid 40. 300 MHz $^1$H NMR (CDCl$_3$, ppm) δ 7.73 (2 H, d, J=8.4 Hz) 7.45-7.30 (2 H, m) 5.8-5.6 (2 H, m) 5.4-5.3 (2 H, m) 4.3-4.1 (1 H, m) 3.57 (1 H, d, J=9.7 Hz) 3.1-2.9 (2 H, m) 2.5-1.9 (10 H, m) 1.7-1.6 (2 H, m) 1.09 (3 H, s) 0.89 (3 H, s).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid (high R$_f$ diastereomer, 41). The same procedure as above for the 36 was used to give 9 mg (0.018 mmol, 85%) of acid 41. 300 MHz $^1$H NMR (CDCl$_3$, ppm) 7.73 (2 H, d, J=8.8 Hz) 7.45-7.30 (2 H, m) 5.8-5.6 (2 H, m) 5.45-5.30 (2 H, m) 4.3-4.2 (1 H, m) 3.61 (1 H, d, J=9.7 Hz) 3.1-3.0 (2 H, m) 2.5-1.9 (10 H, m) 1.7-1.6 (2 H, m) 1.10 (3 H, s) 0.90 (3 H, s).

2-Benzo[b]thiophen-2-yl-ethanol (9-2, FIG. 9) n-BuLi (100 mL, 160 mmol, 1.6M/hexanes) was added to a −78° C. mixture of thianaphthene (17.31 g, 129 mmol) in THF (70 mL)/ether (30 mL). The mixture was stirred at −78° C. for 2 h and then a solution of ethylene oxide (42.86 g, 1,071 mmol) in THF (70 mL)/ether (30 mL) was added by cannula over 15 min. The resulting mixture was stirred for 2 h at −78° C. and then at room temperature for 15 h. At this time, the mixture was evaporated, 200 mL H$_2$O was added, and the resulting mixture was extracted with ethyl acetate (3×150 mL). The combined organic solution was washed with brine and then was dried (Na$_2$SO$_4$), filtered, and evaporated. Purificaion by flash chromatography on silica gel (20% ethyl acetate/hexanes) gave 8-2 (13.61 g, 78 mmol, 60%).

Benzo[b]thiophen-2-yl-acetaldehyde (9-3). A 0° C. mixture of 9-2 (8.019 g, 44 9 mmol) in 100 mL dichloromethane was treated with Dess-Martin reagent (20 g, 47.2 mmol). The mixture was stirred at 0° C. for 10 min. and at room temperature for 40 min. Saturated NaHCO$_3$ solution (200 mL) and 0.1 M NaHSO$_3$ solution were added and the resulting mixture was extracted with ethyl acetate (3×300 mL). The combined organic solution was dried (Na$_2$SO$_4$), filtered and evaporated to give 9-3 (8.77 g). The aldehyde was taken on crude for the next reaction.

1-Benzo[b]thiophen-2-yl-but-3-yn-2-ol (9-4). A solution of crude 9-3 (8.77 g) in THF (100 mL) was added to a solution of ethynylmagnesium bromide (450 mL, 225 mmol, 0.5 M/THF) at 0° C. by cannula. The mixture was stirred for 1 h at 0° C. and for 1 h at room temperature. The reaction was then queched by addition of 200 mL saturated NH$_4$Cl solution. The layers were separated and the aqueous layer was extracted with ethyl acetate (3×200 mL). The combined organic solution was washed with brine and then was dried (Na$_2$SO$_4$), filtered and evaporated. Purification by flash chromatography on silica gel (10%→20% ethyl acetate/hexanes) gave 8-4 (7.67 g, 37.9 mmol, 84% from 9-2).

(1-Benzo[b]thiophen-2-ylmethyl-prop-2-ynyloxy)-tert-butyl-dimethyl-silane (9-5). DMAP (2.306 g, 18.9 mmol), TBSCl (11.502 g, 76.3 mmol) and triethylamine (5.25 mL, 37.7 mmol) were added to a solution of 9-4 (7.67 g, 37 9 mmol) in dichloromethane (120 mL). After 17 h, 150 mL of saturated NH$_4$Cl solution was added and the layers were separated. The aqueous layer was extracted with dichloromethane (3×100 mL) and the combined organic solution was dried (Na$_2$SO$_4$), filtered and evaporated. Purification by flash chromatography on silica gel (4% ethyl acetate/hexanes) gave 9-5 (8.38 g, 26.5 mmol, 70%).

((E)-1-Benzo[b]thiophen-2-ylmethyl-3-iodo-allyloxy)-tert-butyl-dimethyl-silane (9-6). Cp$_2$ZrHCl (1.719 g, 6.67 mmol) was added to a solution of 9-5 (1.372 g, 4.34 mmol) in dichloromethane (30 mL). The reaction was stirred for 30 min. at room temperature and N-iodosuccinimide (1.997 g, 8.88 mmol) was added. After 1 h, the reaction was poured into 100 mL of saturated NaHCO$_3$ solution. The resulting mixture was extracted with dichloromethane (3×75 mL) and the combined organic extracts were dried (Na$_2$SO$_4$), filtered and evaporated. Purification by flash chromatography on silica gel (2% ethyl acetate/hexanes) gave 9-6 (1.7484 g, 91%).

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid (2-hydroxy-ethyl)-amide (65)—General procedure for synthesis of secondary and tertiary amides. A solution of acid 55 (7 mg, 0.015 mmol) in DMF (0.5 mL) was treated with N-hydroxysuccinimide (6.9 mg, 0.056 mmol). The mixture was stirred for 5 minutes and 1-[3-(dimethylamino)propyl]-3-ethylcarbodiimide hydrochloride (EDCI, 20.7 mg, 0.11 mmol) was added. After stirring for 7 h, 2-aminoethanol (5 L, 0.083 mmol) was added and the mixture stirred further for 16 h. Ethyl acetate (50 mL) was added and the mixture was washed with water (3×50 mL) and brine (50 mL). The organic layer was dried (Na$_2$SO$_4$), filtered and evaporated. Purification by flash chromatography on silica gel (5% methanol/dichloromethane) followed by preparative thin layer chromatography (10% methanol/dichloromethane) gave amide 65 (5 mg, 0.010 mmol, 65%). Amides 60-63 were prepared in a similar manner.

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid amide (69). A solution of acid 55 (9 mg, 0.02 mmol) in dichloromethane (0.2 mL) was treated with triethylamine (15 L, 0.11 mmol). The solution was cooled to 0° C. and after 10 minutes, ethyl chloroformate (7 L, 0.073 mmol) was added. The solution was stirred further for 1 h at 0° C. and then concentrated aqueous ammonium hydroxide solution was added (10 L, 0.26 mmol). The reaction was allowed to stir at room temperature overnight and then was quenched by addition of 0.5 M HCl (7 mL). The mixture was extracted with ethyl acetate (3×30 mL) and the combined ethyl acetate solution was washed with saturated NaHCO$_3$ solution (20 mL) and brine (20 mL) and then was dried (Na$_2$SO$_4$), filtered and evaporated. Purification by flash chromatography on silica gel (2% -6% methanol/dichloromethane) gave the title amide (2.6 mg, 28%).

The methods of screening the compounds of this invention for the desired biological activity are illustrated in the following non-limiting examples. Results for example compounds of this invention are included in Table 2. These results are presented purely for illustrative purposes and are not intended to limit the scope of the invention in any way.

Radioligand Binding

Cells Stably Expressing EP$_1$, EP$_2$, EP$_3$, EP$_4$ and FP Receptors

HEK-293 cells stably expressing the human or feline FP receptor, or EP$_1$, EP$_2$, EP$_3$, or EP$_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM MgCl$_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H—] 17-phenyl PGF$_{2\alpha}$ (5 nM) were performed in a 100 µl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour. Non-specific binding was determined with 10 uM unlabeled 17-phenyl PGF$_{2\alpha}$.

[$^3$H—] PGE$_2$ (5 nM; specific activity 180 Ci mmol) was used as the radioligand for EP receptors. Binding studies employing EP$_1$, EP$_2$, EP$_3$, EP$_4$ were performed in duplicate in at least three separate experiments. A 200 µl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Non-specific binding determined with 10$^{-5}$M of unlabeled PGE$_2$.

Methods for FLIPR™ Studies
(a) Cell Culture

HEK-293(EBNA) cells, stably expressing one type or subtype of recombinant human prostaglandin receptors (prostaglandin receptors expressed: hDP/Gqs5; hEP$_1$; hEP$_2$/Gqs5; hEP$_{3A}$/Gqi5; hEP$_4$/Gqs5; hFP; hIP; hTP), were cultured in 100 mm culture dishes in high-glucose DMEM medium containing 10% fetal bovine serum, 2 mM 1-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on the FLIPR™

Cells were seeded at a density of $5 \times 10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 μM, plates were washed four times with HBSS-HEPES buffer to remove excess dye leaving 100 μl in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 l volume to each well to give the desired final concentration. The peak increase in fluorescence intensity was recorded for each well. On each plate, four wells each served as negative (HBSS-HEPES buffer) and positive controls (standard agonists: BW245C (hDP); PGE$_2$ (hEP$_1$; hEP$_2$/Gqs5; hEP$_{3A}$/Gqi5; hEP$_4$/Gqs5); PGF$_2$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an n≥3.

TABLE 2

| Compound | hFP | hEP$_1$ | hEP$_2$ | hEP$_{3D}$ hEP$_{3A}$ | hEP$_4$ | hDP | hIP | hTP |
|---|---|---|---|---|---|---|---|---|
| 21 | NA | NA | >10K | NA | 98 | NA | NA | NA |
| 22 | NA | NA | NA | NA | 300 | NA | NA | NA |
|  |  |  | NA | NA | 30 |  |  |  |
| 23 | NA | NA | NA | >10K | 44 | NA | NA | >10K |
|  |  |  | NA | NA | 0.1 |  |  |  |
| 24 | NA | NA | NA | >>10K | 26 | NA | NA | NA |
|  |  |  | NA | NA | 0.1 |  |  |  |
| 34 | NA |  | NA | NA | >10K |  | NA | NA |
|  |  |  |  |  | >10K |  |  |  |
| 35 | NA |  |  | NA | 2455 |  | NA | NA |
| 36 | NA |  | NA | NA | 200 |  | >10K | NA |
|  |  |  |  |  | 66 |  |  |  |
| 37 | NA |  | NA | NA | 100 |  | >10K | NA |
|  |  |  |  |  | 32 |  |  |  |
| 38 | NA |  | NA | NA | 2700 |  | NA | NA |
|  |  |  |  |  | 269 |  |  |  |
| 39 | NA |  | NA | NA | 2300 |  | NA | NA |
|  |  |  |  |  | 141 |  |  |  |
| 40 | NA |  | NA | NA | 200 |  | NA | >10K |
|  |  |  |  |  | 0.3 |  |  |  |
| 41 | NA |  | >10K | NA | 20 |  | NA | >10K |
| 42 | NA | NA | NA | >$10^4$ | >$10^4$ | NA | NA | NA |
|  |  |  | NA | 559 | NA |  |  |  |
| 43 | NA | >$10^4$ | NA | 1700 | 400 |  | 3981 | 18 |
|  |  |  | NA | 11 | 63 |  |  |  |
| 44 | NA | 782 | 1500 | 300 | 5.5 | >10K | 284 | 18 |
|  |  |  | 944 | 4.6 | 0.2 |  |  |  |
| 45 | NA | NA | NA | >$10^4$ | 400 | NA | NA | 631 |
|  |  |  | NA | 531 | 51 |  | NA | NA |
| 46 | NA | 290 | >10K | >10K | 4 | NA | NA |  |
|  |  |  |  | 589 | 0.4 |  |  |  |
| 47 | NA | 963 | NA | >10K | 76 |  | NA |  |
| 48 |  |  |  | NA | 45 |  |  |  |
| 49 |  |  |  | NA | 1400 |  |  |  |
| 50 | NA | 638 | NA | 6607 | 2400 |  | NA | >10K |
|  |  |  |  | >10K | 3162 |  |  |  |
| 51 | NA |  | NA | NA | 700 |  | NA |  |
| 52 | NA | 27 | NA | 60 | 72 |  | NA |  |
|  |  |  |  |  | 18 |  |  |  |
| 53 | NA | 1020 | NA | 1862 | 59 |  | NA |  |
|  |  |  |  |  | 6.4 |  |  |  |
| 54 | NA | 308 | NA | 4700 | 20 | NA | NA |  |
|  |  |  |  | NA | 0.3 |  |  |  |
| 55 | NA | 758 | NA | >10K | 310 | NA | NA |  |
|  |  |  |  | NA | 38 |  |  |  |
| 60 | NA | NA | NA | NA | >10K | NA | NA | NA |

TABLE 2-continued

| Compound | hFP | hEP$_1$ | hEP$_2$ | hEP$_{3D}$ hEP$_{3A}$ | hEP$_4$ | hDP | hIP | hTP |
|---|---|---|---|---|---|---|---|---|
| 61 | NA | NA | NA | NA | NA | NA | NA | NA |
| 62 | NA | NA | NA | NA | 832 | NA | NA | NA |
| 63 | NA | >10K | NA | NA | 478 | NA | NA | NA |
| 64 | NA | NA | NA | NA | 4154 | NA | NA | NA |
| 65 | NA | NA | NA | NA | NA | NA | NA | NA |
| 68 | NA | NA | NA | NA | 678 | NA | NA | >10K |
| 69 | NA | NA | NA | NA | 5000 | NA | NA | >10K |
| 70 | NA | NA | NA | >10K | 219 | NA | NA | |
| 71 | NA | NA | NA | NA | 10000 | NA | NA | |
| 72 | NA | NA | NA | NA | >10K | NA | NA | NA |
| 73 | NA | NA | NA | NA | NA | NA | NA | NA |
| 74 | NA | 2376 | NA | | 256 | NA | NA | |
| 75 | NA | 2050 | NA | | >10K | NA | NA | >10K |

The top numbers are the radioligand binding IC50 values(nM)
The bottom numbers are the functional EC50 data (nM)

While not intending to limit the scope of the invention in any way, the results presented in Table 2 suggest that the compounds described herein are selective EP4 agonists, and will thus be useful for the treatment of inflammatory bowel disease.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and α$_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as Ca$^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chloprostenol, fluprostenol, 13,14-dihydro-chloprostenol, isopropyl unoprostone, latanoprost and the like.

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound represented by Formula I:

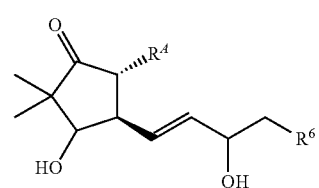

I or a pharmaceutically acceptable salt thereof, wherein:
R$^4$ is selected from the group consisting of:

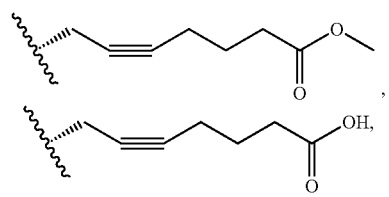

-continued

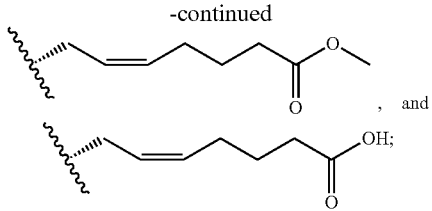
, and and
R⁶ is

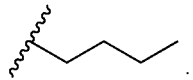 [SMILES: *CCCC]
.

2. The compound according to claim 1, wherein the compound is selected from the group consisting of:

7-[(1R,4S,5R)-4-Hydroxy-5-((E)-(S)-3-hydroxy-oct-1-enyl)-3,3-dimethyl-2-oxo-cyclopentyl]-hept-5-ynoic acid methyl ester;
7-[(1R,4S,5R)-4-Hydroxy-5-((E)-(S)-3-hydroxy-oct-1-enyl)-3,3-dimethyl-2-oxo-cyclopentyl]-hept-5-ynoic acid;
(Z)-7-[(1R,4S,5R)-4-Hydroxy-5-((E)-(S)-3-hydroxy-oct-1-enyl)-3,3-dimethyl-2-oxo-cyclopentyl]-hept-5-enoic acid;
(Z)-7-[(1R,4S,5R)-4-Hydroxy-5-((E)-(S)-3-hydroxy-oct-1-enyl)-3,3-dimethyl-2-oxo-cyclopentyl]-hept-5-enoic acid methyl ester;
or a pharmaceutically acceptable salt thereof.

3. A pharmaceutical composition comprising a compound according to claim 1, or a pharmaceutically acceptable salt thereof, and an pharmaceutically acceptable excipient.

4. A pharmaceutical composition comprising a compound according to claim 2, or a pharmaceutically acceptable salt thereof, and an pharmaceutically acceptable excipient.

* * * * *